US012612354B2

(12) United States Patent
Ouazzani Chahdi et al.

(10) Patent No.: US 12,612,354 B2
(45) Date of Patent: Apr. 28, 2026

(54) CYCLOPENTENONES DERIVATIVES AND THEIR USE AS ANTIBIOTICS

(71) Applicant: Centre National de la Recherche Scientifique (CNRS), Paris (FR)

(72) Inventors: Jamal-Eddine Ouazzani Chahdi, Massy (FR); Géraldine Le Goff, Antony (FR); Jean-Félix Dallery, Beynes (FR); Jean-François Betzer, Saint Remy les Chevresuse (FR); Arnaud Voituriez, Bourg la Reine (FR); Angela Marinetti, Chatenay Malabry (FR); Fanny Cacheux, Plaisance du Touch (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 423 days.

(21) Appl. No.: 18/265,865

(22) PCT Filed: Dec. 9, 2021

(86) PCT No.: PCT/EP2021/085082
§ 371 (c)(1),
(2) Date: Jun. 7, 2023

(87) PCT Pub. No.: WO2022/122975
PCT Pub. Date: Jun. 16, 2022

(65) Prior Publication Data

US 2024/0092716 A1 Mar. 21, 2024

(30) Foreign Application Priority Data

Dec. 9, 2020 (EP) .................................... 20306525

(51) Int. Cl.

| | |
|---|---|
| ***C07C 49/747*** | (2006.01) |
| ***A61P 31/04*** | (2006.01) |
| ***C07C 45/59*** | (2006.01) |
| ***C07C 49/753*** | (2006.01) |
| ***C07C 69/738*** | (2006.01) |
| ***C07D 317/54*** | (2006.01) |

(52) U.S. Cl.

CPC ............ *C07C 49/747* (2013.01); *A61P 31/04* (2018.01); *C07C 45/59* (2013.01); *C07C 49/753* (2013.01); *C07C 69/738* (2013.01); *C07D 317/54* (2013.01); *C07C 2601/10* (2017.05)

(58) Field of Classification Search

CPC ..... C07C 49/747; C07C 49/753; C07C 45/59; C07C 69/738; C07D 317/54
See application file for complete search history.

(56) References Cited

U.S. PATENT DOCUMENTS

| | | | |
|---|---|---|---|
| 2012/0028800 | A1 | 2/2012 | Mathews et al. |
| 2012/0065066 | A1 | 3/2012 | Mathews et al. |
| 2013/0053385 | A1 | 2/2013 | Jeanmart et al. |
| 2017/0121269 | A1 | 5/2017 | Ouazzani et al. |

FOREIGN PATENT DOCUMENTS

| | | | |
|---|---|---|---|
| CN | 107141227 | A | 9/2017 |
| JP | H1143460 | A | 2/1999 |
| JP | 2003532698 | A | 11/2003 |
| JP | 2004533486 | A | 11/2004 |
| JP | 2005511791 | A | 4/2005 |
| JP | 3753438 | B2 | 3/2006 |
| JP | 2012516835 | A | 7/2012 |
| JP | 2012526732 | A | 11/2012 |
| JP | 2013514293 | A | 4/2013 |
| WO | WO-03004479 | A1 | 1/2003 |

(Continued)

OTHER PUBLICATIONS

West et al. (J. Org. Chem. 1993, 58, p. 5043-5044) (Year: 1993).*
Veits et al. (Angew. Chem. Int. Ed. 2010, 49, p. 9484-9487) (Year: 2010).*
Reddy et al. (Tetrahedron Letters, 2012, 53, p. 1776-1779) (Year: 2012).*
Bredihhin et al., *Application of 5-Ethoxymethylfurfural (EMF) for the Production of Cyclopentenones*, 48 Synthesis A—H 2016.

(Continued)

*Primary Examiner* — James D. Anderson
(74) *Attorney, Agent, or Firm* — Panitch Schwarze Belisario & Nadel LLP; Erin M. Dunston

(57) ABSTRACT

The present invention relates to a compound of formula (I) or a pharmaceutically acceptable salt and/or solvate thereof, for use as a drug, especially as an antibiotic. The present invention also relates to a pharmaceutical composition comprising said compound of formula (I) and at least one pharmaceutically acceptable excipient. The present invention further concerns a method of preparation of a compound of formula (I').

(I)

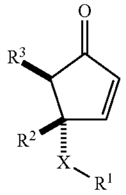

(I')

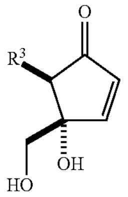

20 Claims, 2 Drawing Sheets

(56) References Cited

FOREIGN PATENT DOCUMENTS

WO WO-03051893 A2 6/2003

OTHER PUBLICATIONS

Figure 1:
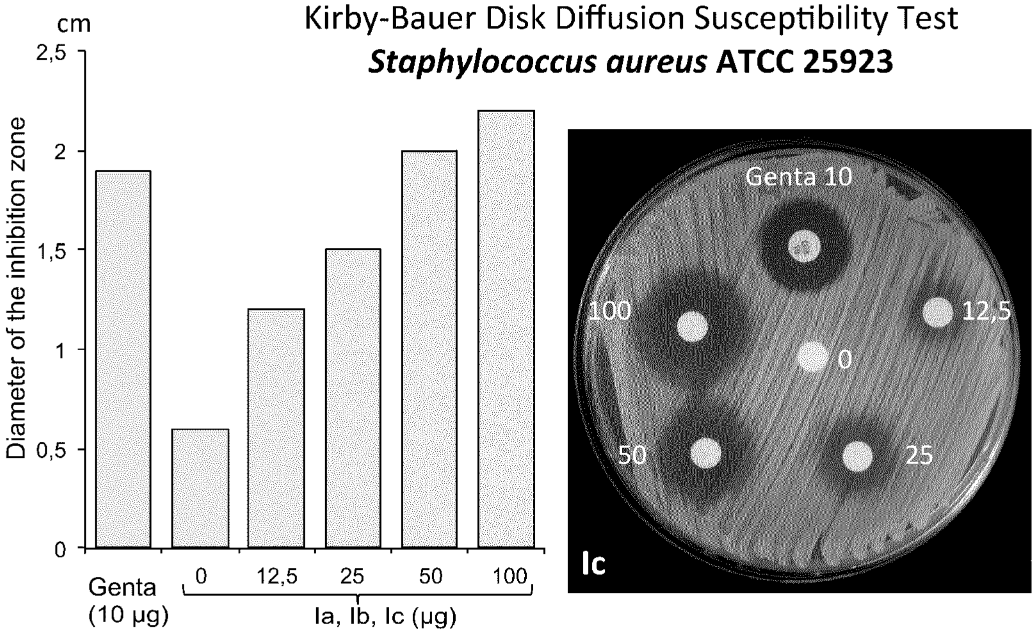

Cai et al., *Catalytic Asymmetric Piancatelli Rearrangement: Brønsted Acid Cataylzed 4π Electrocyclization for the Synthesis of Multisubstituted Cyclopentenones*, 55 Angew. Chem. Int. Ed. 14126-14130 (2016).

D'Auria, *A New Simple Procedure for the Isomerization of 2-Furylcarbinols to Cyclopentenones*, 52(1) Hetrocycles 185-194 (2000).

DeBarardinis et al., *Facile Synthesis of a Family of $H_8$BINOL-Amine Compounds and Catalytic Asymmetric Arylzinc Addition to Aldehydes*, 75 J. Org. Chem. 2836-2850 (2010).

Duan et al., *Synthesis of novel planar chiral Ag and Rh N-heterocyclic carbene complexes derived from [2.2]paracyclophane and their application in ultrasound assisted asymmetric addition reactions of organoboronic acids to aldehydes* 24 Tetrahedron: Asymmetry 241-248 (2013).

European Search Report mailed on May 25, 2021, in counterpart EP Patent Application No. 20306525.

Fisher et al., *Efficient synthesis of 4-hydroxycyclopentenones: dysprosium(III) triflate catalyzed Piancatelli rearrangement*, 70 Tetrahedron 4105-4110 (2014).

Gade et al., *Catalytic Enantioselective Aza-Piancatelli Rearrangement*, 28 Synlett 1096-1100 (2017).

International Search Report issued on Mar. 3, 2022, in counterpart PCT/EP2021/085082.

Kuriyama et al., *Efficient 1,2-Addition of Aryl- and Alkenylboronic Acids to Aldehydes Catalyzed by the Palladium/Thioether-Imidazolinium Chloride System*, 73 J. Org. Chem. 1597-1600 (2008).

Leboefu et al., *Harnessing the Lewis Acidity of HFIP through its Cooperation with a Calcium(II) Salt: Application to the Aza-Piancatelli Reaction*, 22 Chem. Eur. J. 16165-16171 (2016).

Li et al. *Catalytic Enantioselective Aza-Piancatelli Rearrangement*, 55 Angew. Chem. Int. Ed. 15125-15128 (2016).

Nandy et al., *A convenient method for the syntheses of tetrahydrofuran moiety from furan by catalytic transfer of hydrogenation with ammonium formate*, 49 Tetrahedron Letters 2469-2471 (2008).

Notaro et al., *Increasing the Cytotoxicity of Ru(II) Polypyridyl Complexes by tuning the Electronic Structure of Dioxo Ligands*, Journal of the American Society 1-67 (2020).

Palmer et al., *Rapid and Steroselective Synthesis of Spirocyclic Ethers via Intramolecular Piancatelli Rearrangement*, 15(3) Organic Letters 476-479 (2013).

Plutschack et al., *Visible-Light-Mediated Achmatowicz Rearrangement*, Org. Lett. A-D (2016).

Rajmohan et al., *Facile synthesis of 5-hydroxymethylfurfural: A sustainable raw material for synthesis of key intermediates toward 21,23-dioxaporphyrins*, The Royal Society of Chemistry 1-8 (2013).

Riva et al., *Efficient Continuous Flow Synthesis of Hydroxamic Acids and Suberoylanilide Hydroxamic Acid Preparation*, 74 J. Org. Chem. 3540-3543 (2009).

Schober et al., *Catalytic and Enantioselective oxa-Piancatelli Reaction Using Chiral Vanadium Complex*, The Royal Society of Chemistry 1-3 (2012).

Tanami et al., *Phenyl-substituted hydroxycyclopentenons and bone formation promoters containing them*, Caplus 1-3 (1999).

Ulbrich et al., *Microwave- or Microreactor-Assisted Conversion of Furfuryl Alcohols into 4-Hydroxy-2-cyclopentenones*, 13 Synlett 2037-2040 (2010).

Wang et al. *Microwave- or Microreactor-Assisted Conversion of Furfuryl Alcohols into 4-Hydroxy-2-cyclopentenones*, 54 Angew. Chem. Int. 8756-8759 (2015).

Office Action issued in counterpart JP Patent Application No. 2023535375 (with English translation) (Oct. 2, 2025).

* cited by examiner

CYCLOPENTENONES DERIVATIVES AND THEIR USE AS ANTIBIOTICS

CROSS-REFERENCE TO RELATED APPLICATIONS

This application is a U.S. National Stage Application pursuant to 35 U.S.C. § 371 of International Patent Application PCT/EP2021/085082, filed on Dec. 9, 2021, and published as WO 2022/122975 on Jun. 16, 2022, which claims priority to European Patent Application 20306525.5, filed on Dec. 9, 2020, all of which are incorporated herein by reference in their entireties for all purposes.

FIELD OF THE INVENTION

The present invention relates to the use of cyclopentenone derivatives as drugs, in particular as antibiotics. The present invention also concerns new cyclopentanone derivatives and their method of preparation.

BACKGROUND

Infectious diseases are the leading cause of morbidity and mortality worldwide. In particular, many germs are becoming increasingly resistant to known and widely used antibiotics, posing a major public health problem. The WHO indicates that resistance to available antibiotics would lead to 10 million deaths by 2050. One representative example of this type of resistant germ is the MRSA (Methicillin-Resistant *Staphylococcus aureus*).

There is thus a need for new classes of antibiotics active against a broad spectrum of bacteria. Especially, antibiotics showing a selectivity toward gram negative bacteria are sought.

The inventors have thus investigated cyclopentanone derivatives for use as drugs with a broad spectrum of biological activities. Seeking for new class of antibiotics, the inventors have surprisingly discovered that cyclopentanone derivatives of formula (I) show a strong activity against bacteria, especially gram negative bacteria.

The cyclopentenone derivatives disclosed herein have a simple chemical structure and are absent from the catalogue of traditional antibiotics used in the clinic. Access to these molecules is easy and cost-effective. Through their structures, the molecules allow access to various structural analogues and to antibiotic combinations that can offer solutions in cases of infections that are difficult to treat.

SUMMARY

In a first aspect, the present invention relates to a compound of the following formula (I)

(I)

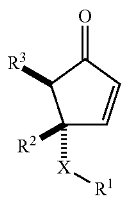

wherein

X is O or NH, $R^1$ is H, an optionally substituted aryl, $C(=O)-C_1-C_6$ alkyl, $C(=O)-O-C_1-C_6$ alkyl or $Si(C_1-C_6\ alkyl)_3$, $R^2$ is H or $CH_2OR^4$, $R^4$ being H, $C_1-C_6$ alkyl, an optionally substituted $C_1-C_6$ alkyl-aryl or $C(=O)R^5$, $R^5$ being an optionally substituted aryl or an optionally substituted heterocycle, or $R^1$ and $R^2$ together represent an optionally substituted heterocycle, and $R^3$ is an optionally substituted aryl or an optionally substituted heteroaryl, as well as any isomers, diastereoisomers, enantiomers and mixtures thereof and any pharmaceutically acceptable salts and/or solvates thereof, provided in said compounds $R^3$ and $X-R^1$ groups are in trans position.

for use as a drug.

In a second aspect, the present invention relates to compound of formula (I) as recited in claims 11, 12 and 13 or a pharmaceutically acceptable salt and/or solvate thereof.

In a third aspect, the present invention concerns a method of preparation of the compounds of formula (I) as described above.

In a fourth aspect, the present invention relates to a pharmaceutical composition comprising at least one pharmaceutically acceptable excipient and at least one compound of formula (I) or a pharmaceutically acceptable salt and/or solvate thereof.

The present invention also relates to the pharmaceutical composition as described above for use as a drug.

Definitions

The term "stereoisomers" as used herein refers to configurational stereoisomers and more particularly to optical isomers.

In the present invention, the optical isomers result in particular from the different position in space of the substituents of a chiral carbon atom. Optical isomers that are not mirror images of one another are thus designated as "diastereoisomers", and optical isomers, which are non-superimposable mirror images are designated as "enantiomers".

An equimolar mixture of two enantiomers of a chiral compound is designated as a racemic mixture or racemate.

The term "pharmaceutically acceptable" as used herein is intended to mean a compound or material that is useful to the preparation of a pharmaceutical composition, and that is generally safe and non-toxic, for a pharmaceutical use.

The term "pharmaceutically acceptable salt and/or solvate" as used herein designates a salt and/or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L25 tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The term "halogen", as used in the present invention, refers to a fluorine, bromine, chlorine or iodine atom.

The term "$C_1$-$C_6$ alkyl", as used herein, refers to a straight or branched monovalent saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "heterocycle" as used herein refers to a non-aromatic, saturated or unsaturated monocycle or polycycle (comprising fused, bridged or spiro rings) comprising preferably 5 to 10, notably 5 or 6, atoms in the ring(s), in which the atoms of the ring(s) consist of carbon atoms and one or more, advantageously 1 to 4, and more advantageously 1 or 2, heteroatoms, such as a nitrogen, oxygen or sulphur atom, the remainder being carbon atoms. A heterocycle can be notably piperidinyl, piperizinyl, pyrrolidinyl, pyrazolidinyl, imidazolidinyl, azepanyl, thiazolidinyl, isothiazolidinyl, oxazocanyl, thiazepanyl, benzimidazolonyl or coumarin of formula:

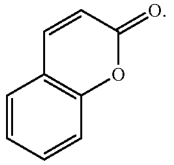 [SMILES: O=c1ccc2ccccc2o1]

The term "aryl" as used herein refers to an aromatic hydrocarbon group preferably comprising from 6 to 14 carbon atoms and comprising one or more fused rings, such as, for example, a phenyl, naphthyl or a phenanthryl group. Advantageously, it is a phenyl group.

The term "$C_1$-$C_6$ alkyl-aryl" as used herein refers to an alkyl as defined above substituted by an aryl group as defined above. An example of "$C_1$-$C_6$ alkyl-aryl" is a benzyl group.

The term "heteroaryl", as used herein, refers to an aromatic group comprising one or several, notably one or two, fused hydrocarbon cycles in which one or several, notably one to four, advantageously one or two, carbon atoms each have been replaced with a heteroatom selected from a sulfur atom, an oxygen atom and a nitrogen atom, preferably selected from an oxygen atom and a nitrogen atom. It can be a furyl, thienyl, pyrrolyl, pyridyl, oxazolyl, isoxazolyl, thiazolyle, isothiazolyl, imidazolyl, pyrazolyl, oxadiazolyl, thiadiazolyl, triazolyl, tetrazolyl, pyridazinyl, pyrimidinyl, pyrazinyl, triazinyl, quinolyl, isoquinolyl, quinoxalyl or indolyl. Preferably, it is a thienyl, thiazolyl or indolyl.

When a group is said to be "optionally substituted", it means that the group is optionally substituted with one or more substituents, typically one to three, which may be selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$ and CN wherein $R^a$ to $R^g$ are, independently of one another, H or $C_1$-$C_6$ alkyl. In some embodiments, two substituents may form together a heterocycle. For instance, a phenyl group can be substituted by two substituents together forming a heterocycle such as a 1,3-dioxolane.

The term "$C_3$-$C_7$ cycloalkyl" as used herein refers to a saturated hydrocarbon ring comprising from 3 to 7 carbons, including cyclopropyl, cyclobutyl, cyclopentyl, cyclohexyl and cycloheptyl.

The term "pharmaceutical composition" as used herein designates a composition having preventive and curative properties towards bacterial infections.

The expression "treatment" is intended to be directed towards all types of animals, preferably mammals, more preferably humans. In the case of a treatment of an animal which is not human kind, it will be referred to a veterinary treatment.

DETAILED DESCRIPTION

Compounds of Formula (I)

Compounds of formula (I) exhibit the following formula:

(I)

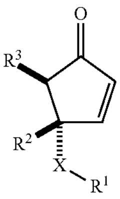

wherein

X is O or NH, $R^1$ is H, an optionally substituted aryl, C(═O)—$C_1$-$C_6$ alkyl, C(═O)—O—$C_1$-$C_6$ alkyl or Si($C_1$-$C_6$ alkyl)$_3$, $R^2$ is H or $CH_2OR^4$ with $R^4$ being H, $C_1$-$C_6$ alkyl, an optionally substituted $C_1$-$C_6$ alkyl-aryl or C(═O)$R^5$ with $R^5$ being an optionally substituted aryl or an optionally substituted heterocycle, or $R^1$ and $R^2$ together represent an optionally substituted heterocycle, and $R^3$ is an optionally substituted aryl or an optionally substituted heteroaryl, as well as any stereoisomers, diastereoisomers, enantiomers and mixtures thereof and any pharmaceutically acceptable salts and/or solvates thereof, provided in said compounds $R^3$ and X—$R^1$ groups are in trans position.

The compounds of formula (I) may be in the form of a mixture of stereoisomers, in particular a racemic mixture thereof.

The compounds of formula (I) can be in the form of a stereoisomer or a mixture of stereoisomers, such as a mixture of enantiomers, for example a racemic mixture. Preferably, the compounds are in the form of a racemic mixture of one diastereoisomer as illustrated in the present application.

Although the compounds of formula (I) may be represented herein below as specific stereoisomers, it has to be understood that the representation encompasses any stereoisomers thereof provided $R^3$ and X—$R^1$ groups are in trans position.

In some embodiments, the substituent $R^2$ represents $CH_2OR^4$ with $R^4$ being H, $C_1$-$C_6$ alkyl, an optionally substituted $C_1$-$C_6$ alkyl-aryl or C(=O)$R^5$ with $R^5$ being an optionally substituted aryl or an optionally substituted heterocycle. In some embodiments, $R^4$ represents H, an optionally substituted benzyl or C(=O)$R^5$ with $R^5$ being an optionally substituted phenyl or a coumarin group. For example, $R^4$ may thus represent H or one of the following groups:

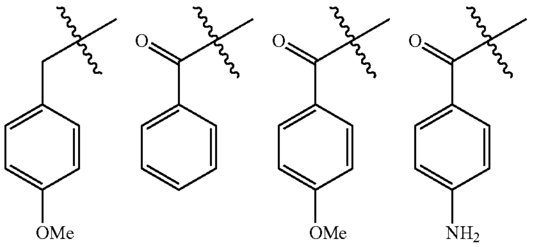

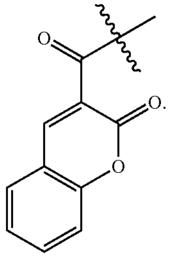

In some preferred embodiments, $R^2$ represents H or $CH_2OH$.

In some preferred embodiments, $R^1$ is H, an optionally substituted phenyl, C(=O)-methyl, C(=O)—O— tert-butyl or a tert-butyldimethylsilyl group. Preferably, $R^1$ is H, C(=O)-methyl or an aryl, said aryl being unsubstituted or substituted with one or more groups selected from halogen, $C_1$-$C_6$ haloalkyl, O—$C_1$-$C_6$alkyl and $C_1$-$C_6$ alkyl. In particular, when $R^1$ is an aryl, it is unsubstituted or substituted with one or two groups independently selected from halogen, $CF_3$ group and OMe group.

In some embodiments, X is NH. When X is a NH group, $R^1$ is preferably an aryl as defined above.

In some embodiments, X is an oxygen atom. When X is an oxygen atom, $R^1$ is preferably H or C(=O)-methyl, more preferably H.

Advantageously, $R^1$ is H or C(=O)—$C_1$-$C_6$ alkyl, preferably H or C(=O)-methyl, more preferably H.

In some other embodiments, $R^1$ and $R^2$ together represent a heterocycle, such as ethylene oxide or 1,3 dioxolane, being unsubstituted or substituted with one oxo or $C_3$-$C_7$ cycloalkyl such as cyclohexyl.

In some embodiments, $R^1$ is H or C(=O)—$C_1$-$C_6$ alkyl, preferably H or C(=O)-methyl, $R^2$ is H or $CH_2OH$, X is O and $R^3$ is an aryl, preferably a phenyl optionally substituted with one or two groups selected from halogen, fluorine, in particular Cl, $C_1$-$C_6$ alkyl and O—$C_1$-$C_6$ alkyl, in particular methyl or by two substituents together forming a 1,3-dioxolane.

In some embodiments, compounds of formula (I) are compounds in which $R^1$ is H, X is O, $R^2$ is H and $R^3$ is as disclosed herein.

In some embodiments, the compound of formula (I) corresponds to the following formula (I'):

(I')

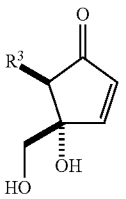

wherein $R^3$ is as disclosed above or below.

Compounds of formula (I') have been found to be highly effective against gram negative bacteria. The compounds of formula (I') may advantageously be selective for gram negative bacteria.

In some embodiments of compounds of formula (I) or (I'), $R^3$ is a heteroaryl, in particular chosen from thienyl, thiazolyl or indolyl, said indolyl being optionally substituted with an alkyl group such as methyl.

In some preferred embodiments of compounds of formula (I) or (I'), $R^3$ is an aryl, such as phenyl, naphthyl or anthracenyl, preferably a phenyl, optionally substituted with one or more, preferably, one to three, groups independently selected from halogen, $C_1$-$C_6$ haloalkyl, $C_1$-$C_6$ alkyl, O—$C_1$-$C_6$ alkyl and CN or by two substituents together forming a heterocycle such as a 1,3-dioxolane. Advantageously, $R^3$ represents a phenyl optionally substituted with one or two groups selected from halogen, in particular F or Cl, $C_1$-$C_6$-alkyl and O—$C_1$-$C_6$ alkyl, in particular methyl or by two substituents together forming a 1,3-dioxolane.

In preferred embodiments, the compound of formula (I) is selected among:

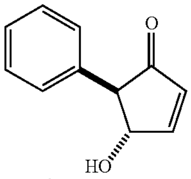

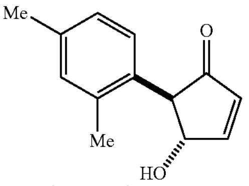

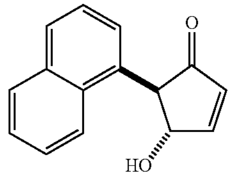

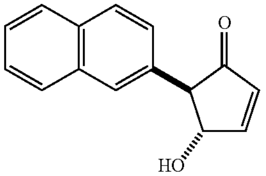

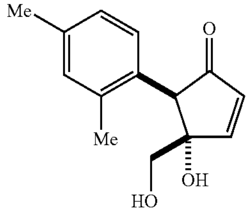

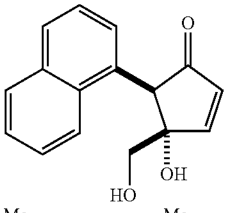

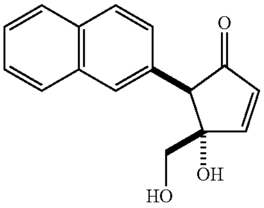

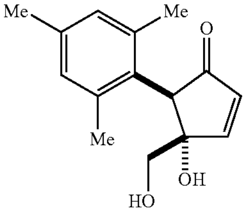

-continued
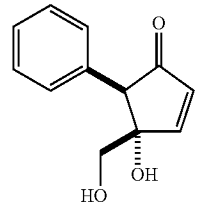
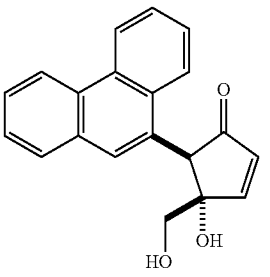
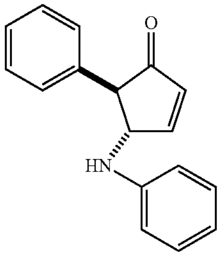
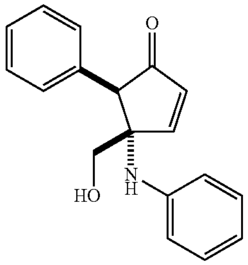
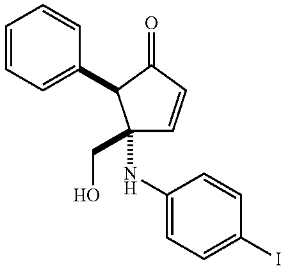
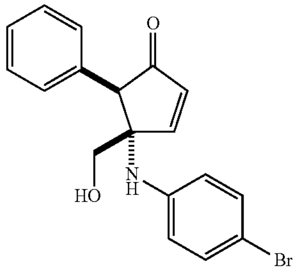
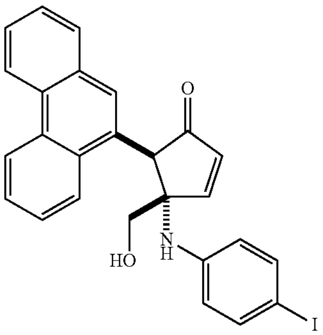
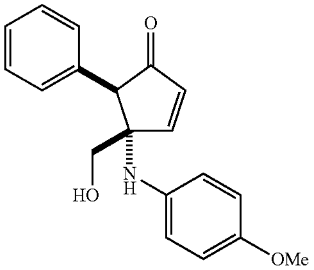
-continued
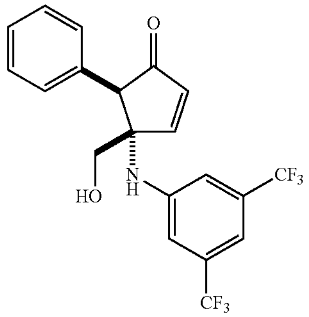
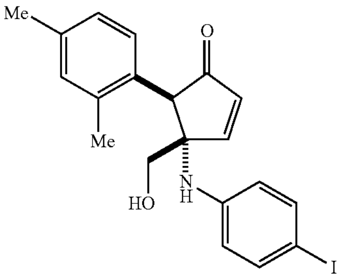
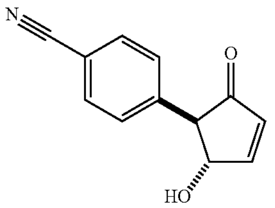
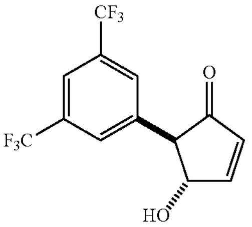
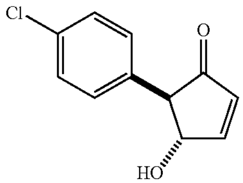
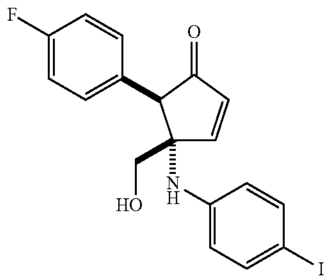
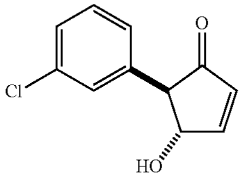
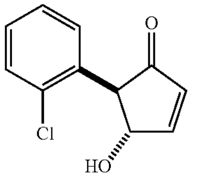
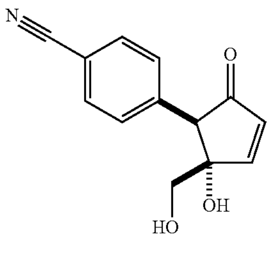
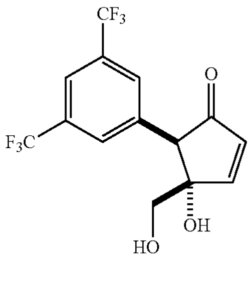

-continued
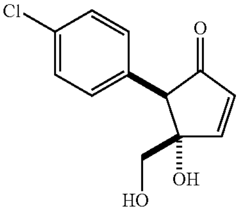
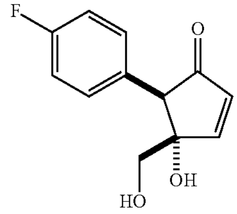
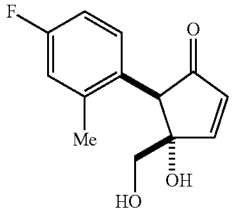
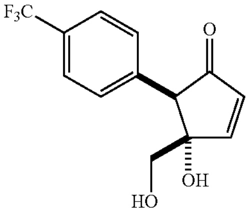
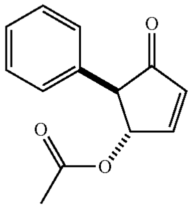
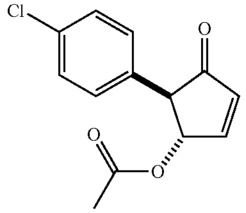
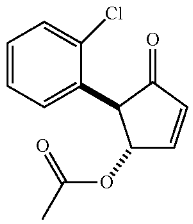
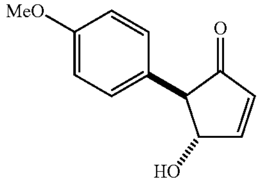
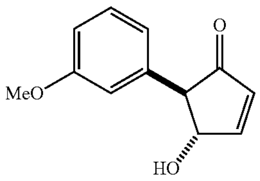
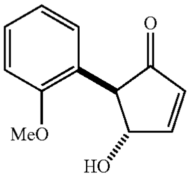
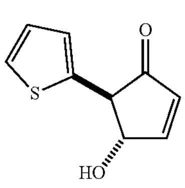
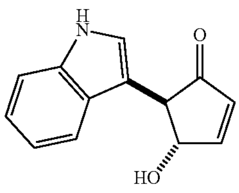
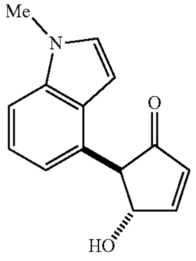
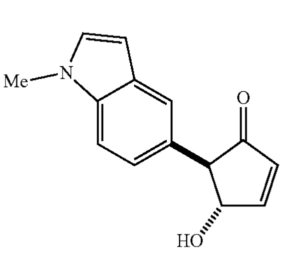
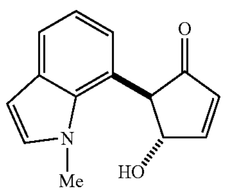
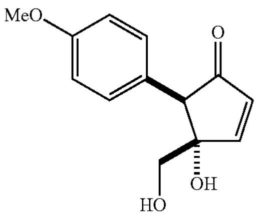
-continued
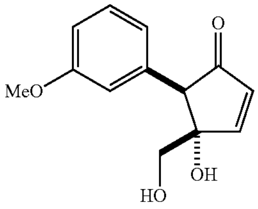
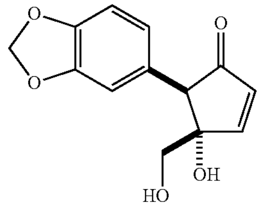
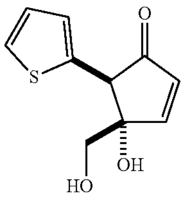
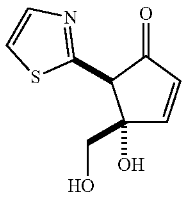
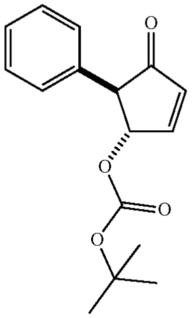
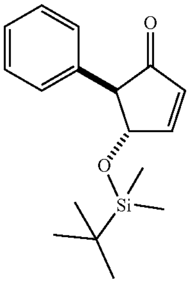
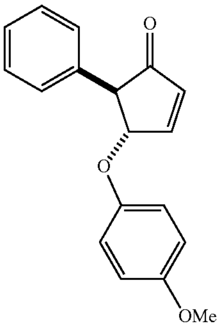
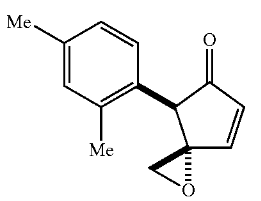
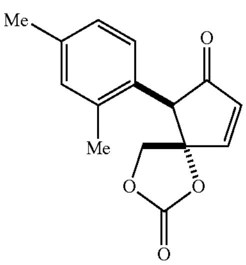
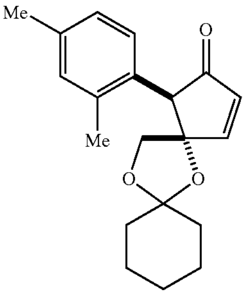

-continued
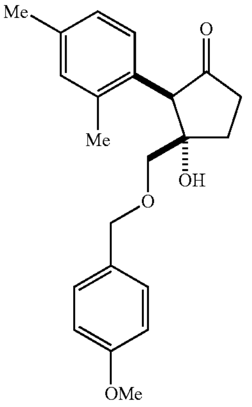
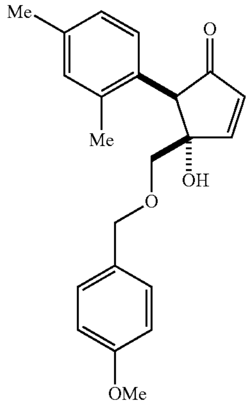
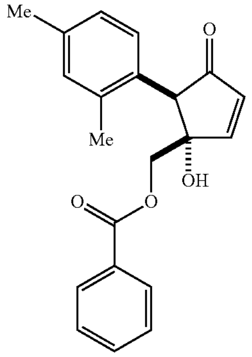
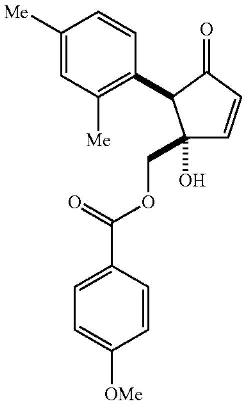
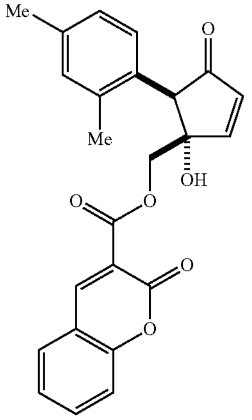
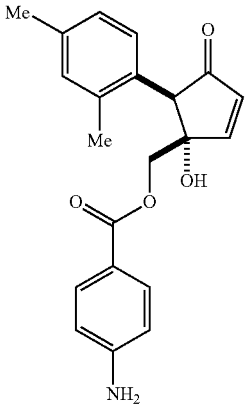
and the pharmaceutically acceptable salt and/or solvate thereof.
More preferably, the compound of formula (I) is selected among:
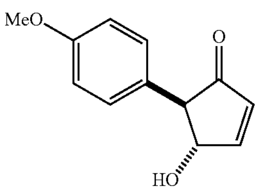
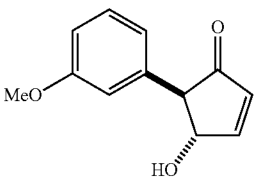
-continued
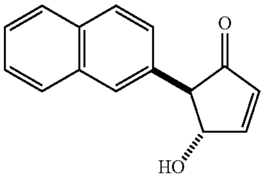
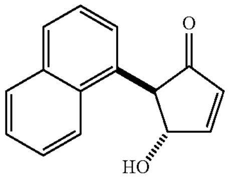
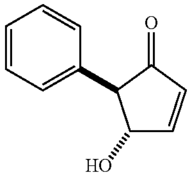
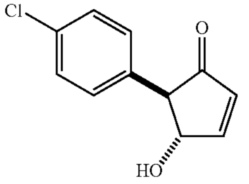
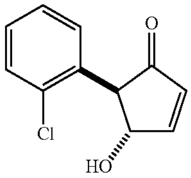
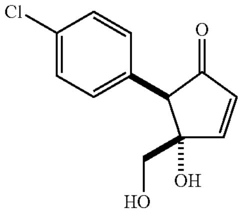
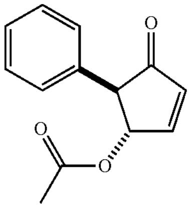
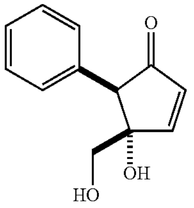
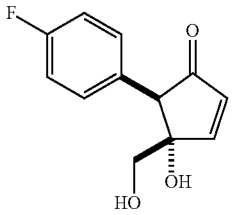
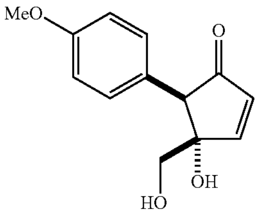
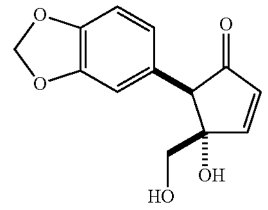
and the pharmaceutically acceptable salt and/or solvate thereof.
More preferably, the compound of formula (I) is selected among:
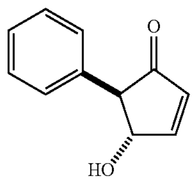
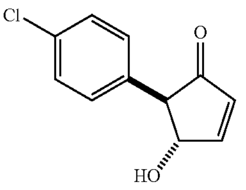

-continued

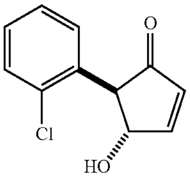
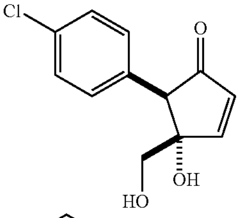
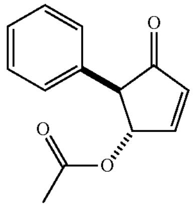
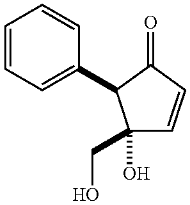
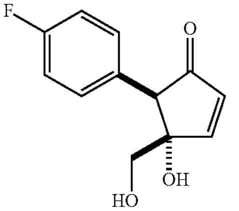
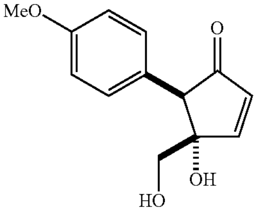
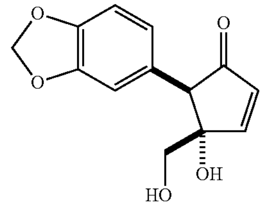

and the pharmaceutically acceptable salt and/or solvate thereof.

Even more preferably, the compound of formula (I) is selected among:

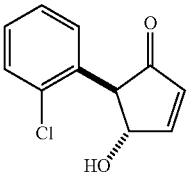
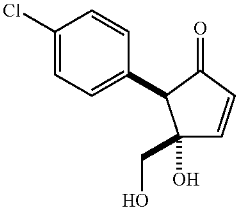
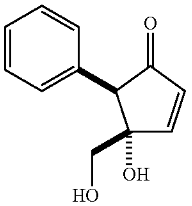
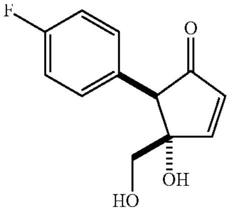
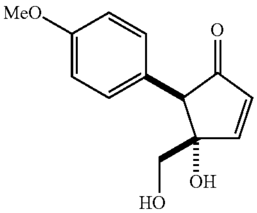
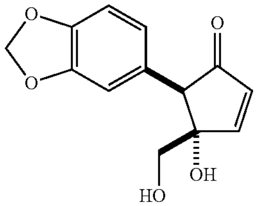

and the pharmaceutically acceptable salt and/or solvate thereof.

In some embodiments, the compound of formula (I) or a pharmaceutically acceptable salt and/or solvate thereof is preferably not one of the following compounds:

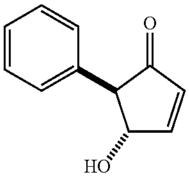
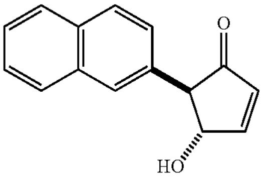
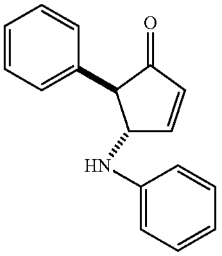
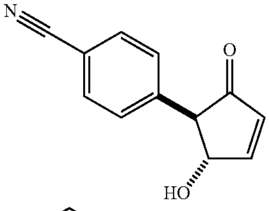
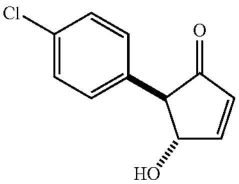
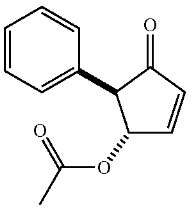

and

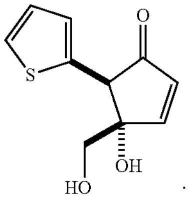

.

In some embodiments, the compound of formula (I) or a pharmaceutically acceptable salt and/or solvate thereof is any of the compounds disclosed in the Examples section, i.e. any of the compounds (Ia) to (Im).

The present invention relates to a compound of formula (I):

(I)

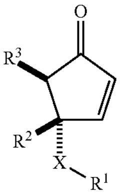

wherein

X is O or NH, $R^1$ is H, an optionally substituted aryl, C(═O)—$C_1$-$C_6$ alkyl, C(═O)—$C_1$-$C_6$ alkyl or Si($C_1$-$C_6$ alkyl)$_3$, $R^2$ is $CH_2OR^4$, $R^4$ being H, an optionally substituted $C_1$-$C_6$ alkyl-aryl or C(═O)$R^5$, $R^5$ being an optionally substituted aryl or an optionally substituted heterocycle, and $R^3$ is an optionally substituted aryl or an optionally substituted heteroaryl, as well as to any stereoisomers, diastereoisomers, enantiomers and mixtures thereof and to any pharmaceutically acceptable salts and/or solvates thereof, provided in said compound $R^3$ and X—$R^1$ groups are in trans position, with the proviso that said compound is not:

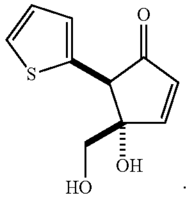

In particular, the present invention relates to compounds If, Ih, Ig and Ii as disclosed in the Examples section.

The present invention also relates to compound (Ic) as disclosed in the Examples section.

Method of Preparation of Compounds of Formula (I)

The present invention relates to a method of preparation of a compound of formula (I) as described above in which X is an oxygen atom, or a pharmaceutically acceptable salt and/or solvate thereof, said method comprising the following steps:

(i) reacting a compound of formula (II)

(II)

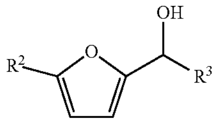

in which $R^2$ and $R^3$ are as defined above, in presence of a $C_1$-$C_6$ alcohol, and optionally a Lewis acid, under heating, (ii) if necessary, isolating the diastereoisomer of formula (I).

Preferably, the compound of formula (II) is selected among:

(II-A)

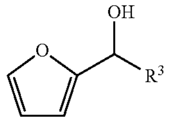

and (II-B)

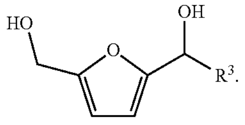

Compound of formula (II) can be obtained using suitable substituents according to methods described in the literature. For example, compounds of formula (II-A) can be obtained starting from furan or 2-furaldehyde according to methods described in Wang, H.-Y.; Yang, K.; Bennett, S. R.; Guo, S.-r.; Tang, W. *Angew. Chem. Int. Ed.* 2015, 54, 8756-8759 and compounds of formula (II-B) can be obtained starting from hydroxymethylfurfural according to methods described in Rajmohan, R.; Gayathri, S.; Vairaprakash, P. *RSC Adv.* 2015, 5, 100401-100407.

Optionally, additional steps of protection/deprotection and/or of functionalization well-known from the skilled person in the art may occur before step (i) to afford compound of formula (II) with substituents $R^2$ and $R^3$ as described above.

The reaction in step (i) is carried out in presence of a $C_1$-$C_6$ alcohol such as methanol, ethanol, propanol, butanol or mixtures thereof, preferably tert-butanol. Advantageously, the $C_1$-$C_6$ alcohol is mixed with water. For example, step (i) is carried out in presence of a tert-butanol/water mixture, in a ratio from 1:1 to 10:1 preferably a ratio of 5:1.

The reaction is preferably carried out under inert atmosphere such as nitrogen ($N_2$) or argon (Ar) atmosphere.

The reaction is preferably carried out at a temperature between 18° C. and 250° C., preferably between 80° C. to 100° C. The heating can be achieved in conventional conditions or with a micro wave. Preferably, the reaction is carried out in a micro wave, which allows to divide the reaction time by ten.

Advantageously, the step (i) is carried out in presence of a Lewis acid, preferably selected in the group consisting of $DyCl_3$, $Dy(OTf)_3$, $Fe(OTf)_3$, $FeCl_3{\cdot}6H_2O$, $ZnCl_2$, $CuCl_2$, $Sc(OTf)_3$ and combinations thereof. More preferably, the Lewis acid is $DyCl_3$.

Step (i) affords a compound of formula (I) in which X is an oxygen atom, $R^1$ is H and $R^2$ and $R^3$ are as defined above.

Therefore, the method of preparation may comprise an additional step between step (i) and step (ii) of functionalization well-known from the skilled person in the art to replace H by another group as defined above on the position of $R^1$.

The final compound obtained can be isolated, i.e. separated from the reaction medium in step (ii) by methods well known to the person skilled in the art, such as by extraction, evaporation of the solvent or by precipitation or crystallization (followed by filtration).

The compound can be also purified if necessary, by methods well known to the person skilled in the art, such as by recrystallisation, by distillation, by chromatography on a column of silica gel or by high performance liquid chromatography (HPLC).

According to another embodiment, the present invention relates to a method of preparation of a compound of formula (I) as described above in which X is a NH group, or a pharmaceutically acceptable salt and/or solvate thereof, said method comprising the following steps:

(i') reacting a compound of formula (II)

(II)

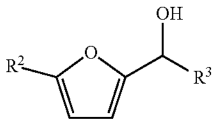

in which $R^2$ and $R^3$ are as defined above, in presence of a $C_1$-$C_6$ alcohol, and optionally a Lewis acid, under heating, with a compound of formula $NH_2$—$R^1$, in which $R^1$ is as defined above, (ii') if necessary, isolating the diastereoisomer of formula (I).

Conditions of steps (I') and (ii') are as defined above for steps (i) and (ii).

According to a preferred embodiment, the present invention relates to a method of preparation of a compound of formula (I') as described above or a pharmaceutically acceptable salt and/or solvate thereof, said method comprising the following steps:

(a) reacting a compound of formula (II-B)

(II-B)

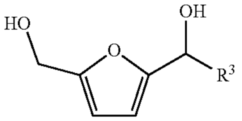

in which $R^2$ and $R^3$ are as defined above, in presence of a $C_1$-$C_6$ alcohol, and optionally a Lewis acid, under a micro wave heating, (b) if necessary, isolating the diastereoisomer of formula (I).

Preferably, the reaction in step (a) is carried out in presence of a tert-butanol/water mixture, in a ratio from 1:1 to 10:1 preferably a ratio of 5:1. The reaction is preferably carried out under inert atmosphere such as nitrogen ($N_2$) or argon (Ar) atmosphere.

The reaction is preferably carried out at a temperature between between 80° C. to 100° C., more preferably at 100° C.

Advantageously, the step (a) is carried out in presence of a Lewis acid, preferably selected in the group consisting of $DyCl_3$, $Dy(OTf)_3$, $Fe(OTf)_3$, $FeCl_3.6H_2O$, $ZnCl_2$, $CuCl_2$, $Sc(OTf)_3$ and combination thereof. More preferably, the Lewis acid is $DyCl_3$.

The final compound of formula (I') obtained can be separated from the reaction medium in step (b) by methods well known to the person skilled in the art, such as by extraction, evaporation of the solvent or by precipitation or crystallization (followed by filtration). The compound can be also purified if necessary by methods well known to the person skilled in the art, such as by recrystallisation, by distillation, by chromatography on a column of silica gel or by high performance liquid chromatography (HPLC).

Pharmaceutical Composition

The present invention also relates to a pharmaceutical composition comprising at least one compound of formula (I) as disclosed herein above or a pharmaceutically acceptable salt and/or solvate thereof, and at least one pharmaceutically acceptable excipient.

The pharmaceutical compositions of the invention can be intended to oral or parenteral (e.g. subcutaneous, intramuscular, intravenous) administration, preferably oral or intravenous administration. The active ingredient can be administered in unit forms for administration, mixed with conventional pharmaceutical carriers, to animals, preferably mammals including humans.

For oral administration, the pharmaceutical composition can be in a solid or liquid (solution or suspension) form.

A solid composition can be in the form of tablets, gelatin capsules, powders, granules and the like. In tablets, the active ingredient can be mixed with pharmaceutical vehicle(s) such as gelatin, starch, lactose, magnesium stearate, talc, gum arabic and the like before being compressed.

The tablets may be further coated, notably with sucrose or with other suitable materials, or they may be treated in such a way that they have a prolonged or delayed activity. In powders or granules, the active ingredient can be mixed or granulated with dispersing agents, wetting agents or suspending agents and with flavor correctors or sweeteners. In gelatin capsules, the active ingredient can be introduced into soft or hard gelatin capsules in the form of a powder or granules such as mentioned previously or in the form of a liquid composition such as mentioned below.

A liquid composition can contain the active ingredient together with a sweetener, a taste enhancer or a suitable coloring agent in a solvent such as water. The liquid composition can also be obtained by suspending or dissolving a powder or granules, as mentioned above, in a liquid such as water, juice, milk, etc. It can be for example a syrup or an elixir.

For parenteral administration, the composition can be in the form of an aqueous suspension or solution which may contain suspending agents and/or wetting agents. The composition is advantageously sterile. It can be in the form of an isotonic solution (in particular in comparison to blood).

The compounds of the invention can be used in a pharmaceutical composition at a dose ranging from 0.01 mg to 1000 mg a day, administered in only one dose once a day or in several doses along the day, for example twice a day in equal doses. The daily administered dose is advantageously comprised between 5 mg and 500 mg, and more advantageously between 10 mg and 200 mg. However, it can be necessary to use doses out of these ranges, which could be noticed by the person skilled in the art.

According to a particular embodiment, the compound of formula (I) or a pharmaceutically acceptable salt and/or solvate thereof is present in the pharmaceutical composition in an encapsulated form. It can be encapsulated within polymeric surfactant micelles or liposomes, the polymeric surfactant being for example a polysorbate, such as polysorbate 80. Such an encapsulation can be performed according to methods well-known from the skilled person, in particular according to methods described in Gasser, G. et al., *J. Am. Chem. Soc.* 2020, 142, 6066-6084. The encapsulation is particularly useful for controlled, targeted and/or extended release of compound of formula (I) in the body of the subject in need thereof. In particular, the encapsulation allows to improve the bioavailability of the compound of formula (I) or a pharmaceutically acceptable salt and/or solvate thereof or the pharmaceutical composition of the present invention by increasing its apparent aqueous solubility. The parenteral injection is therefore facilitated.

Treatment

The present invention relates to the compound of formula (I) as disclosed herein above or a pharmaceutically acceptable salt and/or solvate thereof, or a pharmaceutical composition according to the present invention for use as a drug, in particular for the treatment of bacterial infections.

The present invention also relates to the use of a compound of formula (I) according to the invention or a pharmaceutically acceptable salt and/or solvate thereof, or a pharmaceutical composition according to the present invention for the manufacture of a drug, notably for the treatment of a bacterial infections.

The present invention also relates to the use of a compound of formula (I) according to the invention or a pharmaceutically acceptable salt and/or solvate thereof, or a pharmaceutical composition comprising thereof for the treatment of bacterial infections.

The present invention also relates to a method for treating bacterial infections comprising the administration to a person in need thereof of an effective dose of a compound of formula (I) according to the invention or a pharmaceutically acceptable salt and/or solvate thereof, or a pharmaceutical composition according to the present invention.

According to a preferred embodiment, the compound of formula (I) or a pharmaceutically acceptable salt and/or solvate thereof, or the pharmaceutical composition according to the present invention is useful in the treatment of bacterial infections, such as bacterial infections related to resistant pathogenic Gram negative bacteria or Gram positive bacteria. In other terms, the compound of formula (I) or a pharmaceutically acceptable salt and/or solvate thereof, or the pharmaceutical composition according to the present invention is useful as antibiotics, notably broad-spectrum antibiotics, in particular as antibiotics against resistant pathogenic Gram negative bacteria or gram positive bacteria.

The compound of formula (I) or a pharmaceutically acceptable salt and/or solvate thereof, or the pharmaceutical composition according to the present invention may be useful in the treatment of bacterial infections related to resistant pathogenic bacteria responsible for urogenital, respiratory, digestive, neuronal and skin infections.

According to this embodiment, the compound of formula (I) may thus be preferably selected among

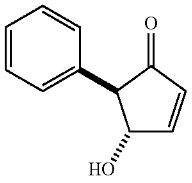
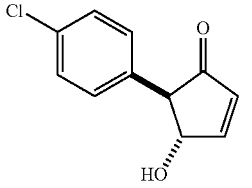
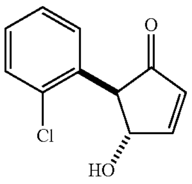
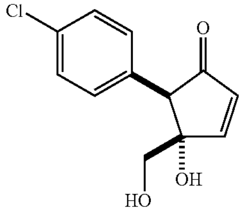
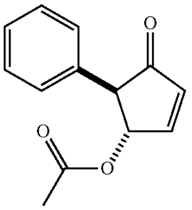
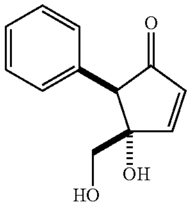
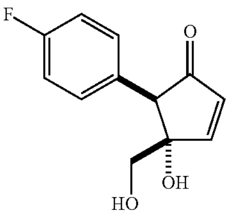
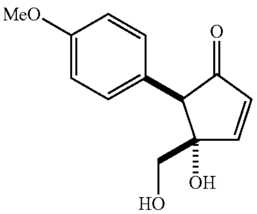

-continued

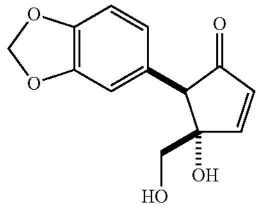

and a pharmaceutically acceptable salt and/or solvate thereof, more preferably among

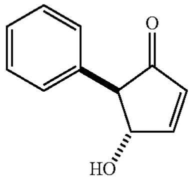
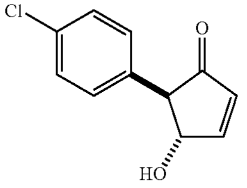
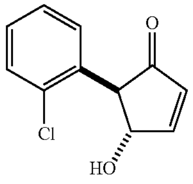
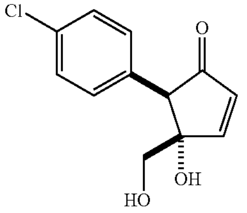
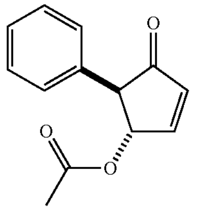

and a pharmaceutically acceptable salt and/or solvate thereof.

For example, bacterial infections may be induced by pathogenic resistant Gram negative bacteria selected from the *Eschericha coli, Enterobacter cloacae, Acinetobacter baumanii* or by pathogenic resistant Gram positive bacteria such as *Staphylococcus aureus.*

Preferably, when the compound of formula (I) is used in the treatment of bacterial infections related to resistant pathogenic Gram negative bacteria, $R^1$ represents H, $R^2$ represents H or $CH_2OR^4$, $R^4$ being preferably H or $C_1$-$C_6$ alkyl, and X and $R^3$ are as defined above. More preferably, $R^1$ represents H, $R^2$ represents H or $CH_2OH$, X represents O and $R^3$ is as defined above. Even more preferably, according to this embodiment, the compound of formula (I) is selected among:

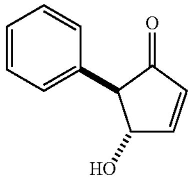
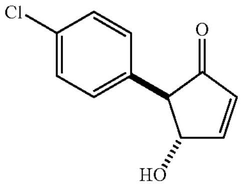

-continued

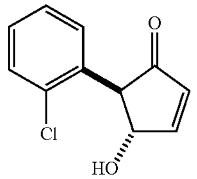

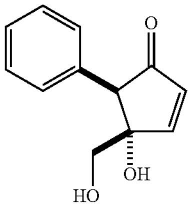

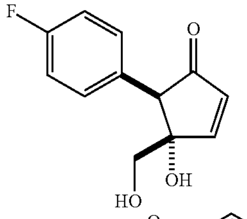

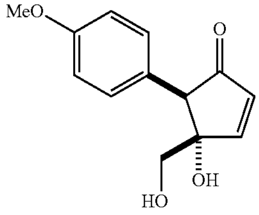

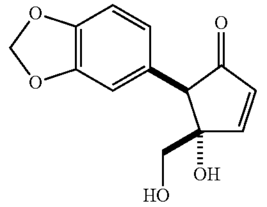

and a pharmaceutically acceptable salt and/or solvate thereof, in particular among

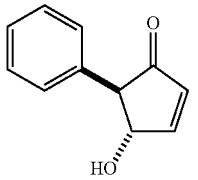

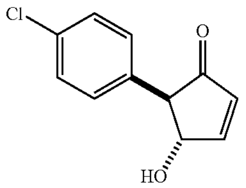

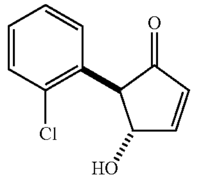

and a pharmaceutically acceptable salt and/or solvate thereof.

Preferably, when the compound of formula (I) is used in the treatment of bacteria infections related to resistant pathogenic Gram positive bacteria, $R^1$ represents H or C(═O)—$C_1$-$C_6$ alkyl, $R^2$ represents H or $CH_2OR^4$, $R^4$ being preferably H or $C_1$-$C_6$ alkyl, X is an oxygen atom and $R^3$ is as defined above. More preferably, $R^1$ represents H or C(═O)-methyl, $R^2$ represents H or $CH_2OH$, X is an oxygen atom and $R^3$ is as defined above. Even more preferably, according to this embodiment, the compound of formula (I) is selected among:

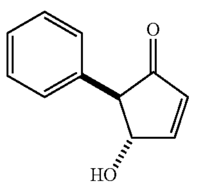

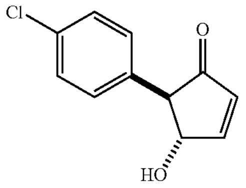

-continued

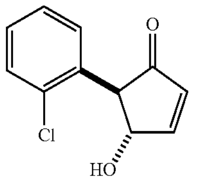

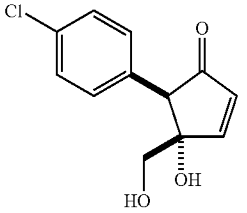

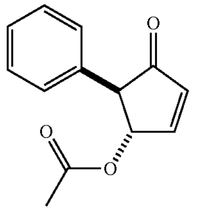

and a pharmaceutically acceptable salt and/or solvate thereof.

According to a particular embodiment, the compound of formula (I) may be selective to the resistant pathogenic Gram negative bacteria. In other terms, it means that the compound of formula (I) may be active against resistant pathogenic Gram negative bacteria while being inert against resistant pathogenic Gram positive bacteria or other pathogenic microorganism.

FIGURES

FIG. 1: Kirby-Bauer Disk diffusion susceptibility test on *Staphylococcus aureus* ATCC 25923 with compounds Ia, Ib and Ic at 12.5, 25, 50 and 100 μg and the reference gentamicin at 10 μg; left: graph representing the diameter of the inhibition zone as a function of each sample; right: photo of the petri dish illustrating the inhibition zones with Ic at 12.5, 25, 50 and 100 μg.

Figure 2:
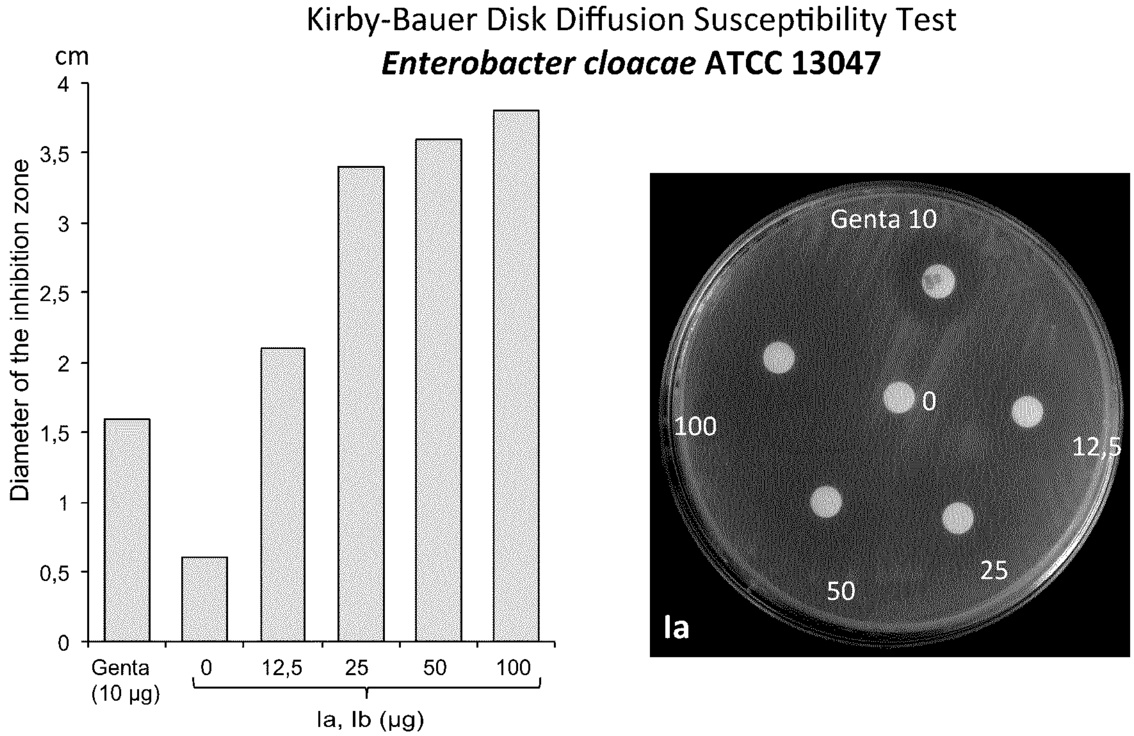

FIG. 2: Kirby-Bauer Disk diffusion susceptibility test on *Enterobacter cloacae* ATCC 13047 with compounds Ia and Ib at 12.5, 25, 50 and 100 μg and the reference gentamicin at 10 μg; left: graph representing the diameter of the inhibition zone as a function of each sample; right: photo of the petri dish illustrating the inhibition zones with Ia at 12.5, 25, 50 and 100 μg.

Figure 3:
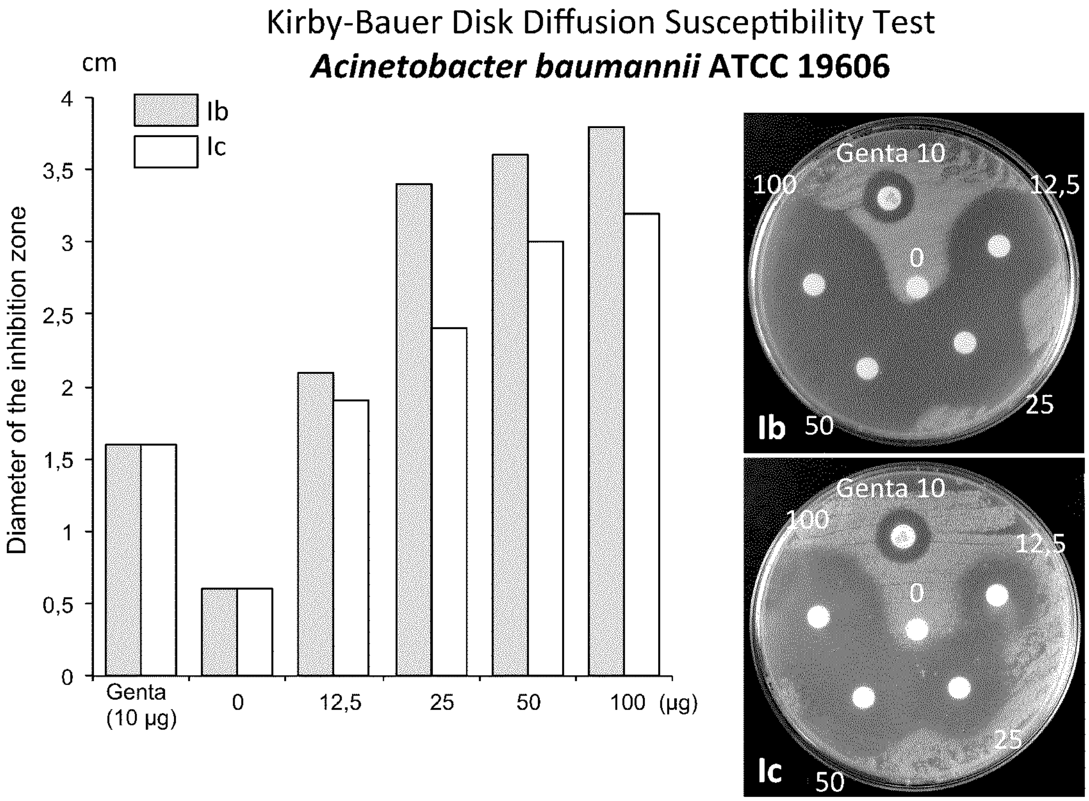

FIG. 3: Kirby-Bauer Disk diffusion susceptibility test on *Acinetobacter baumanii* ATCC 19606 with compounds Ib and Ic at 12.5, 25, 50 and 100 μg and the reference gentamicin at 10 μg; left: graph representing the diameter of the inhibition zone as a function of each sample; right: photo of the petri dish illustrating the inhibition zones with Ib and Ic at 12.5, 25, 50 and 100 μg.

Figure 4:
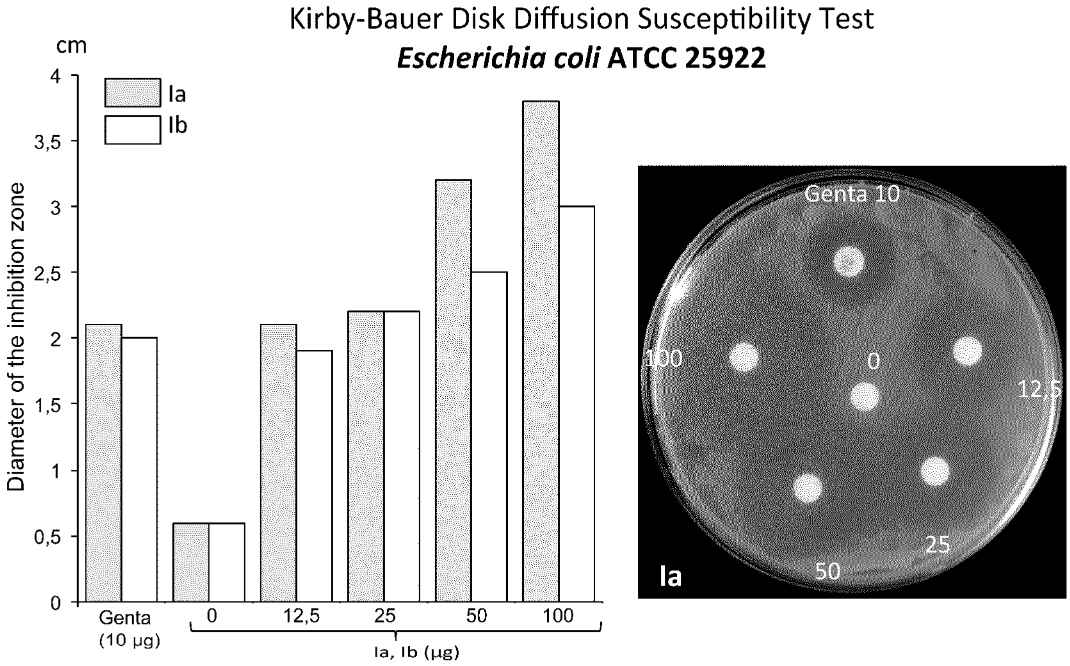

FIG. 4: Kirby-Bauer Disk diffusion susceptibility test on *Escherichia coli* ATCC 25922 with compounds Ia and Ib at 12.5, 25, 50 and 100 μg and the reference gentamicin at 10 μg; left: graph representing the diameter of the inhibition zone as a function of each sample; right: photo of the petri dish illustrating the inhibition zones with Ia at 12.5, 25, 50 and 100 μg.

EXAMPLES

1) Synthesis

Materials, Instrumentation and Methods

Reactions were performed using oven dried glasswares under an atmosphere of argon. All separations were carried out under flash-chromatographic conditions on silica gel (Redi Sep prepacked column, 230-400 mesh) at medium pressure (20 psi) with use of a CombiFlash Companion or preparative HPLC. Reactions were monitored by thin-layer chromatography on Merck silica gel plates (60 F254 aluminum sheets) which were rendered visible by ultraviolet and spraying with vanillin (15%)+sulfuric acid (2.5%) in EtOH followed by heating. Reagent-grade chemicals were obtained from diverse commercial suppliers and used as received.

Microwave-assisted reactions were performed in a Monowave 300 microwave reactor, using borosilicate glass standard vials G10. Sealed reaction vessels were used. The reaction temperature was monitored with an external surface sensor and was maintained in each experiment.

$^1H$ NMR (500 or 300 MHz) and 13C NMR (125 or 75 MHz) spectra were recorded on Brüker Avance spectrometers at 298 K unless otherwise stated. Chemical shifts are given in ppm (δ) and are referenced to the internal solvent signal. Multiplicities are declared as follow: s (singlet), brs (broad singlet), d (doublet), t (triplet), q (quadruplet), dd (doublet of doublet), m (multiplet). Coupling constants J are given in Hz. Carbon multiplicities were determined by DEPT135 experiment.

Infrared spectra (IR) were recorded on a Perkin-Elmer FT-IR system using diamond window Dura SampIIR II and the data are reported in reciprocal centimeters (cm−1).

High-resolution mass spectrometry (HRMS) was performed using electrospray ionization (ESI) and time-of-flight (TOF) analyzer, in positive-ion or negative-ion detection mode.

Synthesis of Intermediates

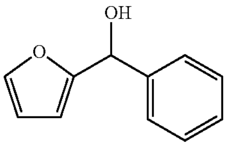

(Furan-2-yl)phenylmethanol

To a solution of 2-furaldehyde (500 mg, 5.20 mmol, 1 equiv.) in anhydrous $Et_2O$ (15 mL) at 0° C. under argon was added phenylmagnesium bromide (1M solution in $Et_2O$, 6.76 mL, 6.76 mmol, 1.3 equiv.). The reaction mixture was stirred 2 h at 0° C. to RT and then quenched by the addition of saturated aqueous $NH_4Cl$ solution (20 mL). The aqueous layer was extracted thrice with ethyl acetate (3×50 mL). The combined organic layers were washed with brine (50 mL), dried over magnesium sulfate, filtered and concentrated to dryness under vacuum. The residue was purified by flash chromatography on silica gel (n-heptane/EtOAc: 100:0 to 70:30) to afford the desired carbinol (900 mg, quant.) as a pale yellow oil. Rf (n-heptane/EtOAc 70:30): 0.42.

The spectral data are consistent to the previous described compound (CAS number [60907-91-7]) in Literature (D'Auria, M. *Heterocycles* 2000, 52, 185-194).

$^1H$ NMR ($CDCl_3$, 500.2 MHz) δ 7.45 (bd, J=7.8 Hz, 2H), 7.40-7.37 (m, 3H), 7.33 (bt, J=7.8 Hz, 2H), 6.32 (dd, J=3.2, 1.8 Hz, 1H), 6.12 (d, J=3.2 Hz, 1H), 5.84 (bs, 1H), 2.38 (bs, 1H). $^{13}C$ NMR ($CDCl_3$, 75.5 MHz) δ 156.1 (C), 142.7 (CH), 140.9 (C), 128.6 (CH), 128.2 (CH), 126.7 (CH), 110.4 (CH), 107.6 (CH), 70.3 (CH).

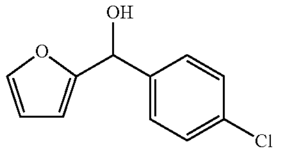

(4-Chlorophenyl)(furan-2-yl)methanol

To a solution of 2-furaldehyde (500 mg, 5.20 mmol, 1 equiv.) in anhydrous $Et_2O$ (15 mL) at 0° C. under argon was added 4-chlorophenylmagnesium bromide (1M solution in $Et_2O$, 6.76 mL, 6.76 mmol, 1.3 equiv.). The reaction mixture was stirred 2 h at 0° C. to RT and then quenched by the addition of saturated aqueous $NH_4Cl$ solution (20 mL). The aqueous layer was extracted thrice with ethyl acetate (3×50 mL). The combined organic layers were washed with brine (50 mL), dried over magnesium sulfate, filtered and concentrated to dryness under vacuum. The residue was purified by flash chromatography on silica gel (n-heptane/EtOAc: 100:0 to 70:30) to afford the desired carbinol (1.08 g, quant.) as a pale yellow oil. Rf (n-heptane/EtOAc 70:30): 0.48.

The spectral data are consistent to the previous described compound (CAS number [143747-66-4]) in Literature (E. Riva, S. Gagliardi, M. Martinelli, D. Passarella, D. Vigo, A. Rencurosi, *Tetrahedron* 2010, 66, 3242-3247).

$^1H$ NMR ($CDCl_3$, 300.2 MHz) δ 7.39 (dd, J=1.8, 0.8 Hz, 1H), 7.37-7.34 (m, 4H), 6.33 (dd, J=3.5, 1.8 Hz, 1H), 6.12 (ddd, J=3.5, 0.8, 0.8 Hz, 1H), 5.81 (bd, J=3.3 Hz, 1H), 2.44 (bd, J=3.3 Hz, 1H). $^{13}C$ NMR ($CDCl_3$, 75.5 MHz) δ 155.6 (C), 142.9 (CH), 139.3 (C), 134.0 (C), 128.8 (CH), 128.1 (CH), 110.4 (CH), 107.7 (CH), 69.6 (CH). IR (n/$cm^{-1}$) 3343, 1596, 1491, 1407, 1225, 1186, 1141, 1089, 1010, 813, 765, 738. HRMS (ESI+) calcd. for $C_{12}H_8OCl$ $[M+H—H_2O]^+$: 191.0264, found: 191.0263.

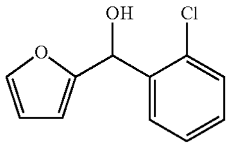

(2-Chlorophenyl)(furan-2-yl)methanol

To a solution of furan (2.20 mL, 30.0 mmol, 2.0 equiv.) in anhydrous $Et_2O$ (60 mL) at 0° C. under argon was added dropwise n-BuLi (2.5M solution in hexane, 7.2 mL, 17.9 mmol, 1.2 equiv). The reaction mixture was stirred for 1 h at 0° C. and 15 min at RT. Then the mixture was cooled at −78° C. and 2-chlorobenzaldehyde (2.10 g, 14.9 mmol, 1.0 equiv.) in anhydrous THF (10 mL) was slowly added and the reaction mixture was stirred for 2 h at −78° C. and 1 h at RT. Then the mixture was quenched by the addition of saturated aqueous $NH_4Cl$ solution (20 mL). The aqueous layer was extracted thrice with ethyl acetate (3×60 mL). The combined organic layers were dried over magnesium sulfate, filtered and concentrated to dryness under vacuum to afford the crude carbinol (2.99 g, 96%) which is used without further purification.

The spectral data are consistent to the previous described compound (CAS number [60907-97-3]) in Literature (M. B. Plutschack, P. H. Seeberger, K. Gilmore, *Organic Letters* 2017, 19, 30-33).

$^1H$ NMR ($CDCl_3$, 500.2 MHz) δ 7.68 (dd, J=7.7, 1.9 Hz, 1H), 7.40 (d, J=2.1 Hz, 1H), 7.36-7.32 (m, 2H), 7.26 (td, J=7.9, 1.9 Hz, 1H), 6.31 (dd, J=3.3, 1.8 Hz, 1H), 6.22 (bd, J=3.1 Hz, 1H), 6.08 (d, J=3.3 Hz, 1H), 2.59 (bd, J=3.1 Hz, 1H).

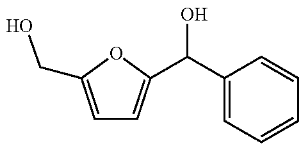

(5-(Hydroxymethyl)furan-2-yl)(phenyl)methanol

To a solution of 5-(hydroxymethyl)furfural (1.00 g, 7.93 mmol, 1.0 eq.) in anhydrous THF (0.25 M), was added at 0° C. a solution of phenylmagnesium bromide (1.0M solution in $Et_2O$, 19.8 mL, 19.8 mmol, 2.5 eq.). The reaction mixture was stirred for 2 h from 0° C. to room temperature. Then the mixture was quenched with a 0.1M solution of hydrogen chloride. The aqueous layer was extracted twice with ethyl acetate. The combined organic layers were washed with brine, dried over magnesium sulfate, filtered and concentrated to dryness under vacuum. The residue was purified by flash chromatography on silica gel (10 to 60% EtOAc/heptane) to afford the desired compound (1.25 g, 77%) as a pale yellow oil. Rf 0.24 (50% EtOAc/heptane).

$^1H$-NMR (Acetone-d6, 300 MHz) δ 7.48-7.44 (m, 2H), 7.37-7.28 (m, 3H), 6.16 (d, 1H, J=3.0 Hz), 6.03 (d, 1H, J=3.0 Hz), 5.75 (d, 1H, J=4.8 Hz), 4.88 (d, J=4.8 Hz, 1H), 4.45 (d, J=5.8 Hz, 2H), 4.11 (t, J=5.8 Hz, 1H); 13C-NMR (Acetone-d6, 75 MHz) δ 157.8 (C), 156.0 (C), 143.5 (C), 128.9 (CH), 128.2 (CH), 127.5 (CH), 108.2 (CH), 108.0 (CH), 70.3 (CH), 57.4 (CH2); IR (ν/cm−1) 3351, 2866, 1494, 1452, 1365, 1189, 1012, 791, 745, 699; HRMS (ESI) m/z=187.0757, calcd. for C12H11O2 [M−H2O+H]+: 187.0759.

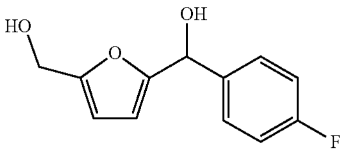

(4-Fluorophenyl)(5-(hydroxymethyl)furan-2-yl)methanol

To a solution of 5-(hydroxymethyl)furfural (450 mg, 3.56 mmol, 1.0 eq.) in anhydrous THF (0.25 M), was added at 0° C. a solution of 4-fluorophenylmagnesium bromide (1.0M solution in THF, 12.5 mL, 12.5 mmol, 3.5 eq.). The reaction mixture was stirred for 2 h from 0° C. to room temperature. Then the mixture was quenched with a 0.1M solution of hydrogen chloride. The aqueous layer was extracted twice with ethyl acetate. The combined organic layers were washed with brine, dried over magnesium sulfate, filtered and concentrated to dryness under vacuum. The residue was purified by flash chromatography on silica gel (10 to 60% EtOAc/heptane) to afford the desired compound (766 mg, 77%) as a pale yellow solid. Rf 0.46 (60% EtOAc/heptane). Mp: 95-98° C.

$^1H$-NMR (Acetone-d6, 300 MHz) δ 7.51-7.47 (m, 2H), 7.13-7.07 (m, 2H), 6.18 (d, J=3.2 Hz, 1H), 6.06 (d, J=3.2 Hz, 1H), 5.78 (d, J=4.8 Hz, 1H), 5.02 (d, J=4.8 Hz, 1H), 4.45 (d, J=6.0 Hz, 2H), 4.19 (t, J=6.0 Hz, 1H); $^{13}C$-NMR (Acetone-d6, 75 MHz) δ 163.0 (d, JCF=240 Hz, C), 157.5 (C), 156.0 (CH), 139.6 (CH), 129.4 (d, JCF=9 Hz, CH), 115.5 (d, JCF=21 Hz, CH), 108.2 (CH), 108.1 (CH), 69.6 (CH), 57.3 (CH2); $^{19}F$-NMR (Acetone-d6, 282 MHz) 60.4; IR (ν/cm−1) 3324, 1604, 1508, 1414, 1221, 1185, 1157, 1011, 843, 800, 777; HRMS (ESI): m/z=205.0655, calcd. for C12H10O2F [M−H2O+H]+: 205.0665.

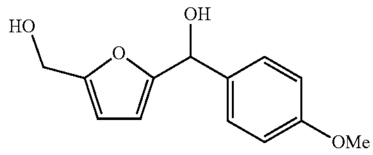

(5-(Hydroxymethyl)furan-2-yl)(4-methoxyphenyl)methanol

To a solution of 5-(hydroxymethyl)furfural (600 mg, 4.76 mmol, 1.0 eq.) in anhydrous THF (0.25 M), was added at 0° C. a solution of 4-methoxyphenylmagnesium bromide (1.0M solution in THF, 16.7 mL, 16.7 mmol, 3.5 eq.). The reaction mixture was stirred for 2 h from 0° C. to room temperature. Then the mixture was quenched with a 0.1M solution of hydrogen chloride. The aqueous layer was extracted twice with ethyl acetate. The combined organic layers were washed with brine, dried over magnesium sulfate, filtered and concentrated to dryness under vacuum. The residue was purified by flash chromatography on silica gel (10 to 60% EtOAc/heptane) to afford the desired compound (1.11 g, 99%) as a pale yellow oil. Rf 0.47 (70% EtOAc/heptane).

$^1H$-NMR (Acetone-d6, 300 MHz) δ 7.35 (d, J=8.4 Hz, 2H), 6.89 (d, J=8.4 Hz, 2H), 6.16 (d, J=3.0 Hz, 1H), 6.03 (d, J=3.0 Hz, 1H), 5.70 (d, J=4.8 Hz, 1H), 4.81 (d, J=4.8 Hz, 1H), 4.44 (d, J=6.0 Hz, 2H), 4.16 (t, J=6.0 Hz, 1H), 3.78 (s, 3H); $^{13}C$-NMR (Acetone-d6, 75 MHz) δ160.0 (C), 158.1 (C), 155.8 (C), 135.6 (C), 128.7 (CH), 114.2 (CH), 108.1 (CH), 107.7 (CH), 70.0 (CH), 57.4 (CH2), 55.5 (CH3); IR (ν/cm−1) 3356, 1611, 1512, 1463, 1303, 1247, 1173, 1012, 838, 800, 781; HRMS (ESI): m/z=217.0863, calcd. for C13H13O3 [M−H2O+H]+: 217.0865.

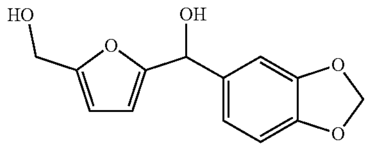

Benzo[d][1,3]dioxol-5-yl(5-(hydroxymethyl)furan-2-yl) methanol

To a suspension of magnesium (462 mg, 19.0 mmol, 6.0 eq) in anhydrous THF (0.20 M) were added a few drops of 5-bromo-1,3-benzodioxole and 1,2-dibromoethane under argon. The reaction mixture was warmed up for 2 minutes to initiate the reaction and 5-bromo-1,3-benzodioxole (2.55 g, 12.7 mmol, 4.0 eq) was added dropwise. After refluxing for 2 h under argon, the mixture was cooled to 0° C. and a solution of 5-(hydroxymethyl)furfural (400 mg, 3.17 mol, 1.0 eq) in THF was added dropwise. After stirring for 2 h from 0° C. to room temperature, the reaction was quenched with a saturated solution of $NH_4Cl$. The aqueous layer was extracted thrice with ethyl acetate. The combined organic layers were washed with brine, dried over magnesium sulfate, filtered and concentrated to dryness under vacuum. The residue was purified by flash chromatography on silica gel (10 to 60% EtOAc/heptane) to afford the desired compound (262 mg, 33%) as a pale yellow solid. Rf 0.24 (50% EtOAc/heptane). Mp: 90-92° C.

$^1$H-NMR (Acetone-d6, 300 MHz) δ 6.96 (d, J=1.5 Hz, 1H), 6.93 (dd, J=8.0, 1.5 Hz, 1H), 6.79 (d, J=8.0 Hz, 1H), 6.17 (d, J=3.0 Hz, 1H), 6.07 (d, J=3.0 Hz, 1H), 5.97 (s, 2H), 5.68 (d, J=4.6 Hz, 1H), 4.86 (d, J=4.6 Hz, 1H), 4.45 (d, J=6.0 Hz, 2H), 4.14 (t, J=6.0 Hz, 1H); $^{13}$C-NMR (Acetone-d6, 75 MHz) δ 157.8 (C), 155.9 (C), 148.5 (C), 147.8 (C), 137.6 (C), 120.9 (CH), 108.5 (CH), 108.2 (CH), 108.0 (CH), 107.7 (CH), 101.9 (CH2), 70.1 (CH), 57.3 (CH2); IR (v/cm−1) 3329, 1502, 1488, 1443, 1242, 1095, 1036, 1011, 928, 868, 776; HRMS (ESI): m/z=231.0665, calcd. for C13H11O4 [M−H2O+H]+: 231.0657.

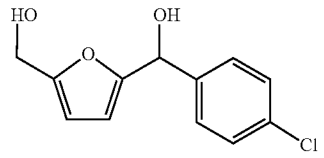

(4-Chlorophenyl)[5-(hydroxymethyl)furan-2yl]methanol

To a solution of hydroxymethylfurfural (HMF) (500 mg, 3.96 mmol, 1 equiv.) in anhydrous THF (15 mL) at 0° C. under argon was added 4-chlorophenylmagnesium bromide (1M solution in $Et_2O$, 9.90 mL, 6.76 mmol, 2.5 equiv.). The reaction mixture was stirred 2 h at 0° C. to RT. Then the mixture was quenched by the addition of aqueous 1M HCl solution (15 mL). The aqueous layer was extracted thrice with ethyl acetate (3×20 mL). The combined organic layers were washed with brine (50 mL), dried over magnesium sulfate, filtered and concentrated to dryness under vacuum. The residue was purified by flash chromatography on silica gel (n-heptane/EtOAc: 100:0 to 50:50) to afford the desired biscarbinol (773 mg, 82%) as a pale yellow solid. Rf (n-heptane/EtOAc 50:50): 0.31.

$^1$H-NMR (Acetone-$d_6$, 300.2 MHz) δ 7.47 (d, J=8.2 Hz, 2H), 7.37 (d, J=8.2 Hz, 2H), 6.18 (d, J=3.2 Hz, 1H), 6.07 (d, J=3.2 Hz, 1H), 5.78 (d, J=4.8 Hz, 1H), 5.09 (d, J=4.8 Hz, 1H), 4.45 (d, J=5.8 Hz, 2H), 4.20 (t, J=5.8 Hz, 1H). $^{13}$C-NMR (Acetone-$d_6$, 75.5 MHz) δ 157.2 (C), 156.2 (C), 142.4 (C), 133.4 (C), 129.2 (CH), 129.0 (CH), 108.3 (CH), 108.2 (CH), 69.6 (CH), 57.3 ($CH_2$). IR (v/$cm^{-1}$) 3350, 2871, 1666, 1490, 1408, 1189, 1089, 1013, 843, 799, 774. HRMS (ESI+): m/z=221.0364, calcd. for $C_{12}H_{10}O_2Cl$ [M+H—$H_2O]^+$: 221.0369.

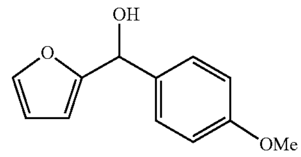

(Furan-2-yl)(4-methoxyphenyl)methanol

To a solution of 4-bromoanisole (500 mg, 2.67 mmol, 1.0 equiv.) in anhydrous THF (15 mL) at −78° C. under argon was added dropwise n-BuLi (1.6 M solution in hexane, 1.8 mL, 2.94 mmol, 1.1 equiv.). The reaction mixture was stirred at −78° C. for 30 min and furaldehyde (0.23 mL, 2.81 mmol, 1.05 equiv.) was added. The reaction mixture was stirred 2 h at −78° C. and quenched with a saturated solution of $NH_4Cl$ (10 mL). The aqueous layer was extracted thrice with ethyl acetate (3×50 mL). The combined organic layers were washed with brine (100 mL), dried over magnesium sulfate, filtered and concentrated to dryness under vacuum. The residue was purified by flash chromatography on silica gel (n-heptane/EtOAc: 100:0 to 60:40) to afford the desired compound (443 mg, 81%) as a pale orange oil. Rf (n-heptane/EtOAc 70:30): 0.27.

The spectral data are consistent to the previous described compound (CAS number [100518-86-3]) in Literature (Nandy, S. K.; Liu, J.; Padmapriya, A. A. *Tetrahedron Lett.* 2008, 49, 2469-2471).

$^1$H NMR ($CDCl_3$, 500 MHz): 7.39 (bs, 1H), 7.36 (d, J=8.6 Hz, 2H), 6.90 (d, J=8.6 Hz, 2H), 6.32-6.31 (m, 1H), 6.12 (d, J=3.3 Hz, 1H), 5.79 (d, J=3.3 Hz, 1H), 3.81 (s, 3H). IR (v/cm−$^1$): 1739, 1610, 1511, 1463, 1303, 1248, 1175, 1032, 838, 742. HRMS (ESI): m/z=187.0751, calcd. for $C_{12}H_{11}O_2$ [M−$H_2$O+H]$^+$: 187.0759.

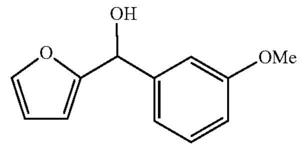

(Furan-2-yl)(3-methoxyphenyl)methanol

Furfural (150 mg, 1.56 mmol, 1.0 equiv.), 3-methoxybenzeneboronic acid (474 mg, 3.12 mmol, 2.0 equiv.), acetylacetonato)dicarbonylrhodium[1] (12 mg, 0.04 mmol, 3 mol %), 1,1'-ferrocenediyl-bis(diphenylphosphine) (26 mg, 0.04 mmol, 3 mol %) were dissolved in DME (5 mL) and water (3 mL) under argon. The reaction mixture was stirred at 80° C. for 16 h. The aqueous layer was extracted thrice with ethyl acetate (10 mL). The combined organic layers were washed with brine, dried over magnesium sulfate, filtered and concentrated to dryness under vacuum. The residue was purified by flash chromatography on silica gel (n-heptane/ethyl acetate). The residue was purified by flash chromatography on silica gel (n-heptane/EtOAc: 100:0 to 40:60) to afford the desired compound (278 mg, 87%) as a pale orange oil. Rf (n-heptane/EtOAc 70:30): 0.27.

The spectral data are consistent to the previous described compound (CAS number [944523-02-8]) in Literature (DeBerardinis, A. M.; Turlington, M.; Ko, J.; Sole, L.; Pu, L. *J. Org. Chem.* 2010, 75, 2836-2850).

$^1$H NMR ($CDCl_3$, 300 MHz): δ 7.39 (dd, J=1.8, 0.9 Hz, 1H), 7.29 (t, J=7.6 Hz, 1H), 7.02-6.99 (m, 2H), 6.88-6.84 (m, 1H), 6.32 (dd, J=3.0, 1.8 Hz, 1H), 6.14 (dd, J=3.0, 0.9 Hz, 1H), 5.81 (bs, 1H), 3.81 (s, 3H). $^{13}$C NMR ($CDCl_3$, 75 MHz): δ 159.9 (C), 155.9 (C), 142.7 (CH), 142.6 (C), 129.6 (CH), 119.0 (CH), 113.8 (CH), 112.0 (CH), 110.4 (CH), 107.6 (CH), 70.2 (CH), 55.4 ($CH_3$). IR (v/cm−$^1$): 3419, 1585, 1489, 1464, 1454, 1434, 1255, 1143, 1037, 1009, 882, 748, 694. HRMS (ESI): m/z=187.0737, calcd. for $C_{12}H_{11}O_2$ [M−$H_2$O+H]$^+$: 187.0759.

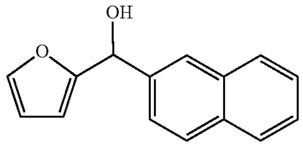

(Furan-2-yl)(naphthalen-2-yl)methanol

To a solution of 2-bromonaphthalene (600 mg, 2.90 mmol, 1.0 equiv.) in anhydrous THF (25 mL) at −78° C. under argon was added dropwise n-BuLi (1.6 M solution in hexane, 4.0 mL, 6.37 mmol, 2.2 equiv.). The reaction mixture was stirred at −78° C. for 30 min and furaldehyde (0.31 mL, 3.77 mmol, 1.3 equiv.) was added. The reaction mixture was stirred 3 h at −78° C. and quenched with a saturated solution of $NH_4Cl$ (10 mL). The aqueous layer was extracted thrice with ethyl acetate (3×50 mL). The combined organic layers were washed with brine (100 mL), dried over magnesium sulfate, filtered and concentrated to dryness under vacuum. The residue was purified by flash chromatography on silica gel (n-heptane/EtOAc: 100:0 to 30:70) to afford the desired compound (309 mg, 48%) as a pale orange oil. Rf (n-heptane/EtOAc 50:50): 0.39.

The spectral data are consistent to the previous described compound (CAS number [944649-38-1]) in Literature (Kuriyama, M.; Shimazawa, R.; Shirai, R. *J. Org. Chem.* 2008, 73, 1597-1600).

$^1$H NMR (Acetone-$d_6$, 300 MHz): δ 8.01 (s, 1H), 7.92-7.86 (m, 3H), 7.60 (dd, J=1.7, 8.6 Hz, 1H), 7.58-7.45 (m, 3H), 6.36 (dd, J=3.3, 1.7 Hz, 1H), 6.23 (dd, J=3.3, 0.7 Hz, 1H), 6.01 (d, J=4.5 Hz, 1H), 5.15 (d, J=4.5 Hz, 1H). $^{13}$C NMR (Acetone-$d_6$, 75 MHz): δ 158.3 (C), 143.0 (CH), 141.0 (C), 134.2 (C), 133.9 (C), 128.8 (CH), 128.5 (CH), 128.3 (CH), 126.9 (CH), 126.6 (CH), 125.9 (CH), 125.8 (CH), 110.9 (CH), 107.4 (CH), 70.3 (CH). IR (ν/cm−$^1$): 3371, 1738, 1602, 1508, 1365, 1217, 1142, 1122, 1010, 782, 742. HRMS (ESI): m/z=207.0814, calcd. for $C_{15}H_{11}O$ $[M-H_2O+H]^+$: 207.0810.

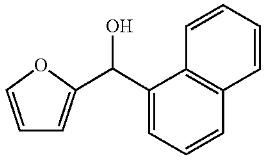

(Furan-2-yl)(naphthalen-1-yl)methanol

Furfural (250 mg, 2.60 mmol, 1.0 equiv.), 1-naphthaleneboronic acid (895 mg, 5.20 mmol, 2.0 equiv.), acetylacetonato)dicarbonylrhodium$^{(I)}$ (20 mg, 0.08 mmol, 3 mol %), 1,1'-ferrocenediyl-bis(diphenylphosphine) (43 mg, 0.08 mmol, 3 mol %) were dissolved in DME (6 mL) and water (4 mL) under argon. The reaction mixture was stirred at 80° C. for 16 h. The aqueous layer was extracted thrice with ethyl acetate (15 mL). The combined organic layers were washed with brine, dried over magnesium sulfate, filtered and concentrated to dryness under vacuum. The residue was purified by flash chromatography on silica gel (n-heptane/ethyl acetate). The residue was purified by flash chromatography on silica gel (n-heptane/EtOAc: 100:0 to 50:50) to afford the desired compound (450 mg, 77%) as a pale yellow oil. Rf (n-heptane/EtOAc 50:50): 0.48.

The spectral data are consistent to the previous described compound (CAS number [873974-71-1]) in Literature (Duan, W.; Ma, Y.; He, F.; Zhao, L.; Chen, J.; Song, C. *Tetrahedron Asym.* 2013, 24, 241-248).

$^1$H NMR (Acetone-$d_6$, 300 MHz): δ 8.16-8.13 (m, 1H), 7.93-7.85 (m, 2H), 7.81 (d, J=7.3 Hz, 1H), 7.55-7.44 (m, 4H), 6.55 (d, J=4.6 Hz, 1H), 6.32 (dd, J=3.3, 1.9 Hz, 1H), 6.13 (d, J=3.3 Hz, 1H), 5.13 (d, J=4.6 Hz, 1H). $^{13}$C NMR (Acetone-$d_6$, 75 MHz): δ 158.2 (C), 142.8 (CH), 138.8 (C), 134.8 (C), 131.7 (C), 129.4 (CH), 128.9 (CH), 126.6 (CH), 126.3 (CH), 126.2 (CH), 125.2 (CH), 124.9 (CH), 111.0 (CH), 107.8 (CH), 67.7 (CH). IR (ν/cm−$^1$): 3379, 3051, 1757, 1687, 1598, 1510, 1220, 1173, 1141, 1054, 1010, 783. HRMS (ESI): m/z=207.0815, calcd. for $C_{15}H_{11}O$ $[M-H_2O+H]^+$: 207.0810.

Synthesis of Compounds of Formula (I)

General Procedure A

To a solution a suitable intermediate (1 eq.) in a mixture of t-BuOH/H2O 5:1 (0.1 M), was added DyCl3 (10 mol %). The reaction mixture was heated under MW irradiation for 1.5 h at 100° C. After cooling to room temperature, the mixture was quenched with a saturated solution of NaHCO3. The aqueous layer was extracted thrice with ethyl acetate. The combined organic layers were washed with brine dried over magnesium sulfate, filtered and concentrated to dryness under vacuum. The residue was purified by flash chromatography on silica gel (heptane/ethyl acetate).

(Ia)

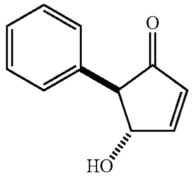

(4S*,5R*)-4-Hydroxy-5-phenyl-cyclopent-2-en-1-one

To a solution of (furan-2-yl)phenylmethanol (1.06 mg, 6.08 mmol, 1 equiv.) in t-BuOH/$H_2O$ 5:1 (0.077M solution, 65 mL and 13 mL respectively) was added $Dy(OTf)_3$ (371 mg, 0.61 mmol, 10 mol %) and the reaction mixture was immediately placed in an oil bath pre-heated to 80° C. The resulting reaction mixture was heated to 80° C. for 18 h. The reaction mixture was cooled to RT and poured into a solution of saturated aqueous $NaHCO_3$. This mixture was extracted thrice with diethyl oxide (3×50 mL). The combined organic layers were washed with brine (30 mL), dried over magnesium sulfate, filtered and concentrated to dryness under vacuum. The residue was purified by flash chromatography on silica gel (n-heptane/EtOAc: 100:0 to 50:50) to afford the desired substituted cyclopentenone Ia (850 mg, 80%) as a pale yellow oil. Rf (n-heptane/EtOAc 40:60): 0.17.

The spectral data are consistent to the previous described compound (CAS number [70951-36-9]) in Literature (Ulbrich, K.; Kreitmeier, P.; Reiser, O. *Synlett* 2010, 2037-2040.).

$^1$H NMR ($CDCl_3$, 500.2 MHz) δ 7.61 (dd, J=5.7, 2.2 Hz, 1H), 7.35 (dd, J=7.5, 7.5 Hz, 2H), 7.29 (d, J=7.5 Hz, 1H), 7.12 (d, J=7.5 Hz, 2H), 6.32 (dd, J=5.7, 1.4 Hz, 1H), 4.97 (bs, 1H), 3.45 (bd, J=2.8 Hz, 1H), 2.57 (bs, 1H). $^{13}$C-NMR ($CDCl_3$, 75.5 MHz) δ 206.3 (CO), 162.7 (CH), 136.9 (C), 134.0 (CH), 128.9 (CH), 128.4 (CH), 127.5 (CH), 78.7 (CH), 62.0 (CH).

(Ib)

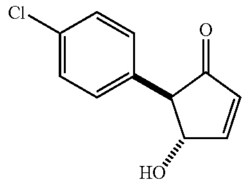

(4S*,5R*)-5-(4-Chlorophenyl)-4-hydroxycyclopent-2-en-1-one

To a solution of (4-chlorophenyl)(furan-2-yl)methanol (340 mg, 1.63 mmol, 1 equiv.) in t-BuOH/$H_2O$ 5:1 (0.077M solution, 18 mL and 3.6 mL respectively) was added $Dy(OTf)_3$ (99.4 mg, 0.16 mmol, 10 mol %) and the reaction mixture was immediately placed in an oil bath pre-heated to 80° C. The resulting reaction mixture was heated to 80° C. for 18 h. The reaction mixture was cooled to RT and poured into a solution of saturated aqueous $NaHCO_3$. This mixture was extracted thrice with diethyl oxide (3×10 mL). The combined organic layers were washed with brine (10 mL), dried over magnesium sulfate, filtered and concentrated to dryness under vacuum. The residue was purified by flash chromatography on silica gel (n-heptane/EtOAc: 100:0 to 50:50) to afford the desired substituted cyclopentenone Ib (242 mg, 71%) as a pale yellow solid. Rf (n-heptane/EtOAc 50:50): 0.25.

The spectral data are consistent to the previous described compound (CAS number [2470798-26-4]) in Literature (Schober, L.; Sako, M.; Takizawa, S.; Gröger, H.; Sasai, H. *Chem. Comm.* 2020, 56, 10151-10154.)

$^1H$ NMR ($CDCl_3$, 500.2 MHz) δ 7.63 (dd, J=5.8, 2.2 Hz, 1H), 7.33 (d, J=8.5 Hz, 2H), 7.09 (d, J=8.5 Hz, 2H), 6.35 (dd, J=5.8, 1.4 Hz, 1H), 4.98 (bs, 1H), 3.45 (bd, J=3.0 Hz, 1H), 2.26 (bs, 1H). $^{13}C$-NMR ($CDCl_3$, 75.5 MHz) δ 204.8 (CO), 161.8 (CH), 135.3 (C), 134.5 (CH), 133.6 (C), 129.8 (CH), 129.2 (CH), 78.9 (CH), 61.5 (CH). IR (ν/$cm^{-1}$) 3395, 1698, 1590, 1492, 1409, 1338, 1182, 1161, 1091, 1033, 1014, 878, 814, 775. HRMS (ESI+): m/z=209.0361, calcd. for $C_{11}H_{10}O_2Cl$ $[M+H]^+$: 209.0369.

(Ic)

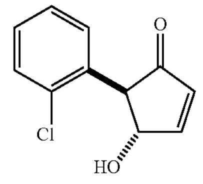

(4S*,5R*)-5-(2-Chlorophenyl)-4-hydroxycyclopent-2-en-1-one

To a solution of (2-chlorophenyl)(furan-2-yl)methanol (342 mg, 1.64 mmol, 1 equiv.) in t-BuOH/$H_2O$ 5:1 (0.077M solution, 18 mL and 3.6 mL respectively) was added $Dy(OTf)_3$ (99.4 mg, 0.16 mmol, 10 mol %) and the reaction mixture was immediately placed in an oil bath pre-heated to 80° C. The resulting reaction mixture was heated to 80° C. for 18 h. The reaction mixture was cooled to RT and poured into a solution of saturated aqueous $NaHCO_3$. This mixture was extracted thrice with diethyl oxide (3×10 mL). The combined organic layers were washed with brine (10 mL), dried over magnesium sulfate, filtered and concentrated to dryness under vacuum. The residue was purified by flash chromatography on silica gel (n-heptane/EtOAc: 100:0 to 50:50) to afford the desired substituted cyclopentenone Ic (236 mg, 69%) as a pale yellow solid. Rf (n-heptane/EtOAc 50:50): 0.30.

$^1H$ NMR ($CDCl_3$, 500.2 MHz) δ 7.60 (dd, J=5.8, 2.2 Hz, 1H), 7.43-7.40 (m, 1H), 7.29-7.25 (m, 2H), 7.15-7.11 (m, 1H), 6.41 (dd, J=5.8, 1.4 Hz, 1H), 5.15 (bs, 1H), 3.77 (bd, J=3.0 Hz, 1H), 2.39 (bs, 1H). $^{13}C$-NMR ($CDCl_3$, 75.5 MHz) δ 204.0 (CO), 160.8 (CH), 134.9 (C), 134.7 (CH), 134.2 (C), 131.6 (CH), 130.2 (CH), 129.2 (CH), 127.4 (CH), 78.1 (CH), 61.4 (CH). IR (ν/$cm^{-1}$) 3404, 1705, 1475, 1444, 1338, 1161, 1107, 1055, 753. HRMS (ESI+): m/z=209.0375, calcd. for $C_{11}H_{10}O_2Cl$ $[M+H]^+$: 209.0369.

(Id)

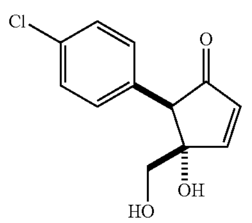

(4S*,5R*)-5-(4-Chlorophenyl)-4-hydroxy-4-(hydroxymethyl)-cyclopent-2-en-1-one

This compound was prepared according to General procedure A using bis-carbinol (4-chlorophenyl)[5-(hydroxymethyl)furan-2-yl]methanol (100 mg, 0.42 mmol, 1 equiv.).

$^1H$ NMR ($CDCl_3$, 300.2 MHz) δ 7.56 (d, J=5.9 Hz, 1H), 7.33 (d, J=8.5 Hz, 2H), 7.11 (d, J=8.5 Hz, 2H), 6.38 (d, J=5.9 Hz, 1H), 3.81 (s, 1H), 3.32 (s, 2H), 1.67 (bs, 1H). $^{13}C$-NMR ($CDCl_3$, 75.5 MHz) δ 204.7 (CO), 162.6 (CH), 134.5 (CH), 134.0 (C), 132.5 (C), 131.1 (CH), 129.2 (CH), 82.0 (C), 66.8 ($CH_2$), 62.6 (CH). IR (ν/$cm^{-1}$) 3404, 2926, 1702, 1592, 1493, 1409, 1339, 1217, 1170, 1091, 1034, 1016, 880. HRMS (ESI+): m/z=239.0479, calcd. for $C_{12}H_{12}O_3Cl$ $[M+H]^+$: 239.0475.

(Ie)

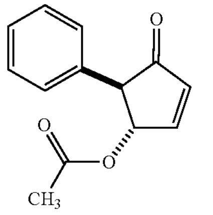

(4S*,5R*)-4-Acetoxy-5-phenyl-cyclopent-2-en-1-one

To a solution of (4S*,5R*)-4-hydroxy-5-phenyl-cyclopent-2-en-1-one (39 mg, 0.22 mmol, 1 equiv.) in acetic anhydride (1.5 mL) at 0° C. was added toluene-4-sulfonic acid monohydrate (2.3 mg, 0.02 mmol, 10 mol %) and the mixture was allowed to warm to RT for 4 hours. Then silica gel (500 mg) was added and acetic anhydride was removed under reduced pressure to provide a solid sample loading for column chromatography. The crude product was purified over silica gel (eluent: n-heptane/EtOAc 0:100 to 3:7) to afford the title compound Ie (38 mg, 79% yield) as a colorless oil. Rf (n-heptane/EtOAc 20:80): 0.38.

$^1H$ NMR ($CDCl_3$, 500.2 MHz) δ 7.69 (dd, J=5.8, 2.3 Hz, 1H), 7.35 (dd, J=7.3, 7.3 Hz, 2H), 7.29 (dd, J=7.3, 7.3 Hz, 1H), 7.15 (d, J=7.3 Hz, 2H), 6.45 (d, J=5.8 Hz, 1H), 5.93 (bs, 1H), 3.59 (d, J=2.3 Hz, 1H), 2.11 (s, 3H). $^{13}C$-NMR ($CDCl_3$, 75.5 MHz) δ 204.0 (CO), 170.3 ($CO_2$), 158.3 (CH), 136.2 (C), 136.1 (CH), 128.9 (CH), 128.1 (CH), 127.6 (CH), 79.4 (CH), 57.6 (CH), 20.8 ($CH_3$). IR (ν/$cm^{-1}$) 3062, 3039, 2943, 1739, 1721, 1498, 1454, 1373, 1325, 1229, 1111, 1078, 1027, 977, 931, 910. HRMS (ESI+): m/z=217.0855, calcd. for $C_{13}H_{13}O_3$ $[M+H]^+$: 217.0865.

(If)

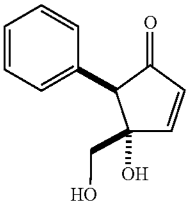

4-Hydroxy-4-(hydroxymethyl)-5-phenylcyclopent-2-en-1-one

This compound was prepared according to the General Procedure A using 50 mg of (5-(Hydroxymethyl)furan-2-yl)(phenyl)methanol (0.25 mmol, 1 equiv.). If (26 mg, 51% yield, dr>95:5) was obtained as a pale yellow oil after flash chromatography (toluene/acetone: 80:20 to 70:30). Rf 0.39 (40% acetone/toluene); $^1$H-NMR ($CDC_3$, 300 MHz) δ 7.53 (d, J=5.8 Hz, 1H), 7.39-7.30 (m, 3H), 7.22-7.16 (m, 2H), 6.40 (d, J=5.8 Hz, 1H), 3.85 (s, 1H), 3.42-3.33 (m, 2H); $^{13}$C-NMR (CDCl3, 75 MHz) δ 205.2 (C), 162.2 (CH), 134.9 (CH), 134.2 (C), 129.7 (CH), 129.3 (CH), 128.1 (CH), 82.1 (C), 66.9 (CH2), 63.6 (CH); IR (ν/cm−1) 3401, 2924, 1699, 1497, 1453, 1338, 1170, 1079, 1033, 925, 814, 739, 699; HRMS (ESI): m/z=205.0876, calcd. for C12H13O3 [M+H]+: 205.0865.

(Ig)

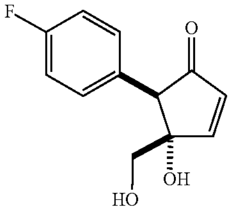

(5-(4-Fluorophenyl)-4-hydroxy-4-(hydroxymethyl)cyclopent-2-en-1-one

This compound was prepared according to the General Procedure A using 60 mg of (4-Fluorophenyl)(5-(hydroxymethyl)furan-2-yl)methanol (0.3 mmol, 1 equiv.). Ig (34 mg, 59% yield, dr=90:10) was obtained as a white solid after flash chromatography (heptane/ethyl acetate: 100:0 to 20:80). Rf 0.31 (60% EtOAc/heptane; Mp: 111-113° C.; $^1$H-NMR (Acetone-d6 300 MHz) δ7.57 (d, J=5.9 Hz, 1H), 7.32-7.27 (m, 2H), 7.10-7.03 (m, 2H), 6.31 (d, J=5.9 Hz, 1H), 4.80 (s, 1H), 3.81 (dd, J=6.3, 4.8 Hz, 1H), 3.77 (s, 1H), 3.30 (dd, J=10.8, 4.8 Hz, 1H), 3.16 (dd, J=10.8, 6.3 Hz, 1H); $^{13}$C-NMR (Acetone-d6, 75 MHz) δ 204.3 (C), 163.7 (CH), 162.7 (d, JCF=241 Hz, C), 134.1 (CH), 133.1 (d, JCF=9 Hz, CH), 132.0 (C), 115.3 (d, JCF=21 Hz, CH), 83.3 (C), 66.1 (CH2), 63.8 (CH); $^{19}$F-NMR (Acetone-d6, 282 MHz) 60.0; IR (ν/cm−1) 3418, 2919, 1704, 1606, 1510, 1225, 1162, 1035, 841, 812; HRMS (ESI): m/z=223.0764, calcd. for C12H12FO3 [M+H]+: 223.0770.

(Ih)

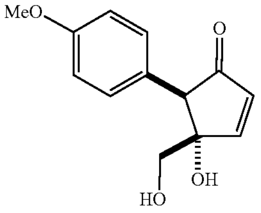

4-Hydroxy-4-(hydroxymethyl)-5-(4-methoxyphenyl)cyclopent-2-en-1-one

This compound was prepared according to the General Procedure A using 70 mg of (5-(Hydroxymethyl)furan-2-yl)(4-methoxyphenyl) methanol (0.3 mmol, 1 equiv.). Ih (25 mg, 35% yield, dr>95:5) was obtained as a pale yellow solid after flash chromatography (heptane/ethyl acetate: 100:0 to 20:80). Rf 0.37 (70% EtOAc/heptane); Mp: 134-136° C.; $^1$H-NMR (CDCl3, 300 MHz) δ7.51 (d, J=5.9 Hz, 1H), 7.07 (d, J=8.8 Hz, 2H), 6.88 (d, J=8.8 Hz, 2H), 6.36 (d, J=5.9 Hz, 1H), 3.79 (s, 3H), 3.77 (s, 1H), 3.38-3.29 (m, 2H); $^{13}$C-NMR ($CDCl_3$, 75 MHz) δ 205.7 (C), 162.4 (CH), 159.3 (C), 134.7 (CH), 130.8 (CH), 125.9 (C), 114.7 (CH), 82.1 (C), 66.9 (CH2), 62.8 (CH), 55.4 (CH3); IR (ν/cm−1) 3411, 2934, 1703, 1612, 1514, 1250, 1180, 1087, 1033, 836; HRMS (ESI): m/z=235.0972, calcd. for C13H15O4 [M+H]+: 235.0970.

(Ii)

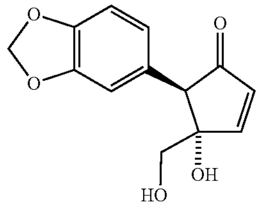

5-(Benzo[d][1,3]dioxol-5-yl)-4-hydroxy-4-(hydroxymethyl)cyclopent-2-en-1-one

This compound was prepared according to the General Procedure A using 74.4 mg of Benzo[d][1,3]dioxol-5-yl(5-(hydroxymethyl)furan-2-yl) methanol (0.30 mmol). Ii (40.4 mg, 54% yield, dr>95:5) was obtained as a brown oil after flash chromatography (heptane/ethyl acetate: 40:60 to 30:70). Rf 0.29 (50% EtOAc/heptane); $^1$H-NMR ($CDCl_3$, 300 MHz) δ 7.52 (d, J=5.8 Hz, 1H), 6.76 (d, J=8.1 Hz, 1H), 6.62 (d, J=8.1 Hz, 1H), 6.60 (s, 1H), 6.33 (d, J=5.8 Hz, 1H), 5.93 (s, 2H), 3.72 (s, 1H), 3.38-3.28 (m, 2H); $^{13}$C-NMR ($CDCl_3$, 75 MHz) δ 205.5 (C), 162.8 (CH), 148.1 (C), 147.3 (C), 134.3 (CH), 127.4 (C), 123.3 (CH), 109.8 (CH), 108.8 (CH), 101.3 (CH2), 82.0 (C), 66.9 (CH2), 63.0 (CH); IR (ν/cm−1) 3411, 2898, 1700, 1504, 1489, 1442, 1234, 1035, 929, 806, 733; HRMS (ESI): m/z=249.0759, calcd. for C13H13O5 [M+H]+: 249.0763.

(Ij)

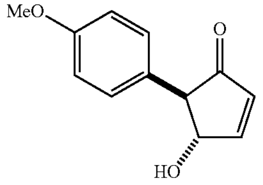

(4S*,5R*)-4-Hydroxy-5-(4-methoxyphenyl)cyclopent-2-en-1-one

To a solution of (furan-2-yl)(4-methoxyphenyl)methanol (80 mg, 0.39 mmol, 1.0 equiv.) in t-BuOH/$H_2O$ 5:1 (0.068 M solution, 5 mL and 0.8 mL respectively) was added $DyCl_3$ (10.5 mg, 0.04 mmol, 10 mol %) and the reaction mixture was immediately placed in an oil bath pre-heated to 80° C. The resulting reaction mixture was heated to 80° C. for 18 h. The reaction mixture was cooled to RT and poured into a solution of saturated aqueous $NaHCO_3$. This mixture was extracted thrice with ethyl acetate (3×10 mL). The combined organic layers were washed with brine (10 mL), dried over magnesium sulfate, filtered and concentrated to dryness under vacuum. The residue was purified by flash chromatography on silica gel (n-heptane/EtOAc: 70:30 to 50:50) to afford the desired substituted cyclopentenone (18 mg, 23%) as a pale yellow oil. Rf (n-heptane/EtOAc 50:50): 0.20.

$^1$H NMR ($CDCl_3$, 300 MHz): δ 7.61 (dd, J=6.0, 2.1 Hz, 1H), 7.06 (d, J=8.0 Hz, 2H), 6.88 (d, J=8.0 Hz, 2H,), 6.33 (dd, J=6.0, 1.5 Hz, 1H), 4.96-4.95 (m, 1H), 3.80 (s, 3H), 3.41 (d, J=3.0 Hz, 1H). $^{13}$C NMR ($CDCl_3$, 75 MHz): δ 205.6 (C), 161.5 (CH), 159.1 (C), 134.7 (CH), 129.5 (CH), 114.6 (CH), 79.3 (CH), 61.7 (CH), 55.5 ($CH_3$). IR (v/cm−$^1$): 3409, 1705, 1613, 1582, 1514, 1302, 1251, 1179, 1033, 825, 762. HRMS (ESI): m/z=205.0865, calcd. for $C_{12}H_{13}O_3$ $[M+H]^+$: 205.0865.

(Ik)

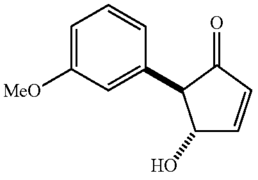

(4S*,5R*)-4-Hydroxy-5-(3-methoxyphenyl)cyclopent-2-en-1-one

To a solution of (furan-2-yl)(3-methoxyphenyl)methanol (60 mg, 0.29 mmol, 1.0 equiv.) in t-BuOH/$H_2O$ 5:1 (0.082 M solution, 3 mL and 0.6 mL respectively) was added $DyCl_3$ (7.9 mg, 0.03 mmol, 10 mol %) and the reaction mixture was immediately placed in an oil bath pre-heated to 80° C. The resulting reaction mixture was heated to 80° C. for 18 h. The reaction mixture was cooled to RT and poured into a solution of saturated aqueous $NaHCO_3$. This mixture was extracted thrice with ethyl acetate (3×10 mL). The combined organic layers were washed with brine (10 mL), dried over magnesium sulfate, filtered and concentrated to dryness under vacuum. The residue was purified by flash chromatography on silica gel (n-heptane/EtOAc: 100:0 to 60:40) to afford the desired substituted cyclopentenone (42 mg, 70%) as a pale yellow oil. Rf (n-heptane/EtOAc 50:50): 0.33. The spectral data are consistent to the previous described compound (CAS number [2470798-31-1]) in Literature (Schober, L.; Sako, M.; Takizawa, S.; Gröger, H.; Sasai, H. *Chem. Comm.* 2020, 56, 10151-10154).

$^1$H NMR ($CDCl_3$, 300 MHz): δ 7.61 (dd, J=5.7, 2.4 Hz, 1H), 7.28 (d, J=8.0 Hz, 1H), 6.83 (ddd, J=8.0, 2.7, 1.2 Hz, 1H), 6.73-6.66 (m, 2H), 6.33 (dd, J=5.7, 1.2 Hz, 1H), 4.98 (bs, 1H), 3.82 (s, 3H), 3.40 (d, J=3.0 Hz, 1H). $^{13}$C NMR ($CDCl_3$, 75 MHz): δ 205.2 (C), 161.8 (CH), 160.1 (C), 138.4 (C), 134.6 (CH), 130.1 (CH), 120.7 (CH), 114.4 (CH), 112.9 (CH), 79.1 (CH), 62.2 (CH), 55.4 ($CH_3$). IR (v/cm−$^1$): 3419, 2940, 1705, 1601, 1584, 1491, 1454, 1437, 1340, 1260, 1157, 1041, 782. HRMS (ESI): m/z=205.0860, calcd. for $C_{12}H_{13}O_3$ $[M+H]^+$: 205.0865.

(Il)

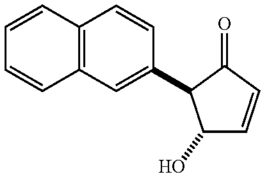

(4S*,5R*)-4-Hydroxy-5-(naphthalen-2-yl)cyclopent-2-en-1-one

To a solution of (furan-2-yl)(naphthalen-2-yl)methanol (80 mg, 0.36 mmol, 1.0 equiv.) in t-BuOH/$H_2O$ 5:1 (0.050 M solution, 6 mL and 1.2 mL respectively) was added $DyCl_3$ (9.6 mg, 0.04 mmol, 10 mol %) and the reaction mixture was immediately placed in an oil bath pre-heated to 80° C. The resulting reaction mixture was heated to 80° C. for 18 h. The reaction mixture was cooled to RT and poured into a solution of saturated aqueous $NaHCO_3$. This mixture was extracted thrice with ethyl acetate (3×10 mL). The combined organic layers were washed with brine (10 mL), dried over magnesium sulfate, filtered and concentrated to dryness under vacuum. The residue was purified by flash chromatography on silica gel (n-heptane/EtOAc: 100:0 to 40:60) to afford the desired substituted cyclopentenone (32 mg, 40%) as a pale orange oil. Rf (n-heptane/EtOAc 50:50): 0.25. The spectral data are consistent to the previous described compound (CAS number [1612765-18-0]) in Literature (Schober, L.; Sako, M.; Takizawa, S.; Gröger, H.; Sasai, H. *Chem. Comm.* 2020, 56, 10151-10154).

$^1$H NMR ($CDCl_3$, 500 MHz): δ 7.81-7.74 (m, 3H), 7.56 (s, 1H), 7.50 (dd, J=5.7, 2.4 Hz, 1H), 7.48-7.46 (m, 2H), 7.07 (dd, J=8.4, 1.9 Hz, 1H), 6.24 (dd, J=5.7, 1.5 Hz, 1H), 4.90 (bs, 1H), 3.49 (d, J=2.9 Hz, 1H). $^{13}$C NMR ($CDCl_3$, 75 MHz): δ 205.8 (C), 162.2 (CH), 138.4 (C), 134.3 (CH), 134.2 (C), 133.5 (C), 132.7 (C), 128.9 (CH), 127.8 (CH), 126.5 (CH), 126.1 (CH), 125.8 (CH), 78.8 (CH), 62.3 (CH). IR (v/cm−$^1$): 3387, 3054, 2919, 1696, 1633, 1599, 1508, 1336, 1156, 1106, 1032, 907, 813. HRMS (ESI): m/z=225.0920, calcd. for $C_{15}H_{13}O_2$ $[M+H]^+$: 225.0916.

(Im)

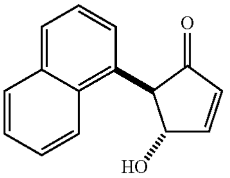

(4S*,5R*)-4-Hydroxy-5-(naphthalen-1-yl)cyclopent-2-en-1-one

To a solution of (furan-2-yl)(naphthalen-1-yl)methanol (100 mg, 0.45 mmol, 1.0 equiv.) in t-BuOH/$H_2O$ 5:1 (0.063 M solution, 6 mL and 1.2 mL respectively) was added $DyCl_3$ (12 mg, 0.05 mmol, 10 mol %) and the reaction mixture was immediately placed in an oil bath pre-heated to 80° C. The resulting reaction mixture was heated to 80° C. for 18 h. The reaction mixture was cooled to RT and poured into a solution of saturated aqueous $NaHCO_3$. This mixture was extracted thrice with ethyl acetate (3×10 mL). The combined organic layers were washed with brine (10 mL), dried over magnesium sulfate, filtered and concentrated to dryness under vacuum. The residue was purified by flash chromatography on silica gel (n-heptane/EtOAc: 100:0 to 50:50) to afford the desired substituted cyclopentenone (99 mg, 99%) as a pale orange oil. Rf (n-heptane/EtOAc 50:50): 0.25. The spectral data are consistent to the previous described compound (CAS number [2470798-35-5]) in Literature (Schober, L.; Sako, M.; Takizawa, S.; Gröger, H.; Sasai, H. *Chem. Comm.* 2020, 56, 10151-10154).

$^1H$ NMR ($CDCl_3$, 300 MHz): δ 7.91-7.86 (m, 1H), 7.81 (d, J=8.1 Hz, 1H), 7.71-7.67 (m, 1H), 7.66 (dd, J=5.8, 2.3 Hz, 1H), 7.53-7.47 (m, 2H), 7.43 (dd, J=8.4, 7.1 Hz, 1H), 7.22 (dd, J=7.1, 1.1 Hz, 1H), 6.48 (dd, J=5.8, 1.4 Hz, 1H), 5.12 (bs, 1H), 4.07 (d, J=2.8 Hz, 1H), 2.41 (bs, 1H). $^{13}C$ NMR ($CDCl_3$, 75 MHz): δ 205.8 (C), 162.1 (CH), 135.0 (CH), 134.4 (C), 133.5 (C), 132.1 (C), 129.3 (CH), 128.5 (CH), 127.3 (CH), 126.7 (CH), 126.0 (CH), 125.7 (CH), 123.6 (CH), 79.0 (CH), 60.5 (CH). IR (ν/cm−$^1$): 3405, 3051, 2920, 1699, 1595, 1510, 1397, 1337, 1158, 1106, 1026, 797, 776, 731. HRMS (ESI): m/z=225.0913, calcd. for $C_{15}H_{13}O_2$ $[M+H]^+$: 225.0916.

2) Antibiotic Activity

Antibiotic activity was evaluated on racemic molecules of trans configuration, on a panel of pathogenic microorganisms.

A. Inhibition Zone Technique (Kirby-Bauer Disk Diffusion Susceptibility Test)

Pre-inoculum Preparation

Pathogenic bacteria were revived by streaking bacteria on 100 mm Petri dishes containing the suitable medium recommended by ATCC protocol, overnight at 30 to 37° C.: Luria-Bertani Broth (LB, Difco, Thermo Fisher Scientific Inc.), Tryptic Soy Broth (TSB, Difco, Thermo Fisher Scientific Inc.), Nutrient Broth (NB, Difco, Thermo Fisher Scientific Inc.), supplemented with 2% of agar (Granulated Agar, Difco, Thermo Fisher Scientific Inc.).

Inoculum Preparation

For each pathogen, several colonies were collected with a loop and transferred in 5 ml of sterile NB medium and incubated on a rotary shaker (130 rpm) overnight at 30 to 37° C.

Assays 150 mm Nutrient Broth Agar plates were swabbed with inocula and kept for 15 min for absorption. Pre-sterilized six-millimeter Whatman No. 1 discs were placed in the Petri dishes and 12.5, 25, 50 and 100 μg of the test compounds in DMSO (10 mg/ml) were applied to the sterile disc papers. The standard drug gentamycin (10 μg) was used as a positive reference standard to determine the sensitivity of each bacterial species and DMSO as a negative control. Then the plates were incubated at 30° or 37° C. for 24 h and inhibition diameters were measured.

Compounds Ia to Ic have also been tested on the following pathogenic bacteria in order to evaluate their inhibition efficacy by the Petri dish inhibition zone method:

*Staphylococcus aureus* ATCC 25923—Gram-positive (compounds Ia, Ib and Ic tested)

*Enterobacter cloacae* ATCC 13047—Gram-negative (compounds Ia and Ib tested)

*Acinetobacter baumannii* ATCC 19606—Gram-negative (compounds Ib and Ic tested)

*Escherichia coli* ATCC 25922—Gram-negative (compounds Ia and Ib tested)

This technique enables to visualize the potential for inhibiting the growth of target pathogenic bacteria. A dose-response study at 12.5, 25, 50 and 100 μg of each compound has been carried out, comparing the inhibition zones with 10 μg gentamicin. The results are shown in FIGS. 1 to 4. All the tested products Ia, Ib and/or Ic show an inhibition activity for each tested pathogenic bacteria. Best results are obtained for Gran negative bacteria, especially *Enterobacter cloacae* as represented on FIG. 2.

Compounds Ib, Ic, Ij, Ik, Il, Im, Ih, Ig, Ii, Id and If have also been tested on the following pathogenic bacteria in order to evaluate their inhibition efficacy by the Petri dish inhibition zone method:

*Micrococcus luteus* ATCC10240;

*Bacillus subtilis* ATCC6633;

*Escherichia coli* ATCC 25922.

The percentage of inhibition growth at 100 μg of each tested compound has been determined. Results are presented in the below table.

| | % inhibition *Micrococcus luteus* | % inhibition *Bacillus subtilis* | % inhibition *Escherichia coli* |
|---|---|---|---|
| Ib | 68% | 51% | 60% |
| Ic | 33% | 31% | 35% |
| Ij | 39% | 61% | 62% |
| Ik | 23% | 48% | 42% |
| Il | 50% | 57% | 40% |
| Im | 51% | 56% | 47% |
| Ih | 0% | 0% | 55% |
| Ig | 0% | 18% | 55% |
| Ii | 0% | 0% | 45% |
| If | 21% | 0% | 57% |
| Id | 0% | 30% | 45% |

B. Minimum Inhibitory Concentration (MIC) Technique

Pre-Inoculum

Pathogenic bacteria were revived by streaking bacteria on 100 mm Petri dishes containing the suitable medium recommended by ATCC protocol, overnight at 30 to 37° C.: Luria-Bertani Broth (LB, Difco, Thermo Fisher Scientific Inc.), Tryptic Soy Broth (TSB, Difco, Thermo Fisher Scientific Inc.), Nutrient Broth (NB, Difco, Thermo Fisher Scientific Inc.), supplemented with 2% of agar (Granulated Agar, Difco, Thermo Fisher Scientific Inc.)

Inoculum Preparation

For each pathogen, several colonies were collected with a loop and transfered in 10 ml of sterile Mueller-Hinton broth (Sigma) medium and incubated on a rotary shaker (130 rpm) for hours at 30 to 37° C. The OD at 600 nm was measured and adjusted to 0.5 OD, then the solution was diluted 400-fold to have the appropriate inoculum Assays The antimicrobial susceptibility was carried out by micro-broth dilution assay. Tests were performed on 96-well plates with 100 μL of Mueller-Hinton broth (Sigma) medium final volume and a final bacterial concentration of $5.10^5$ CUF/ml. The tested compounds were solubilized in dimethyl sulfoxide (DMSO) given 10 mg/mL (then expressed in μM) stock solution. The stock solutions were diluted from 100 μg/ml to 0.195 μg/ml for testing.

Compounds Ia to Ie have also been tested on *Staphylococcus aureus* ATCC 25923 strain and *Staphylococcus aureus* BAA-1766 (MRSA) strain (both Gram-positive) by using the screening method of the measurement of MIC (minimum inhibitory concentration).

This technique enables to determine the minimum concentration that causes total inhibition of the growth of the target pathogen. The table below shows that all product Ia to Ie show a good antibiotic activity. The better antibiotic activity is obtained with molecules Ic and Ie with MIC of 6.25 μg/mL.

| MIC (μg/mL) | Ia | Ib | Ic | Id | Ie |
|---|---|---|---|---|---|
| *S. aureus* ATCC 25923 | 25 | 12.5 | 6.26 | 12 | 6.25 |
| *S. aureus* BAA-1766 | >50 | 18.75 | 37.5 | 12 | 6.25 |

The invention claimed is:

1. A method for treating bacterial infections, comprising administering to a patient in need thereof an effective amount of a compound of the following formula (1) or a pharmaceutical composition comprising a compound of formula (1) and a pharmaceutically acceptable excipient:

(I)

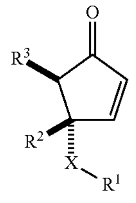

wherein

X is O or NH, $R^1$ is H, C(═O)—$C_1$-$C_6$ alkyl, C(═O)—O—$C_1$-$C_6$ alkyl, Si($C_1$-$C_6$ alkyl)$_3$, or a phenyl optionally substituted with one or more substituents, selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl, $R^2$ is H or $CH_2OR^4$, $R^4$ being H, $C_1$-$C_6$ alkyl, $C_1$-$C_6$ alkyl-substituted by an aryl group optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl or C(═O)$R^5$, $R^5$ being an aryl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^f$, $CO_2R^d$, $CONR^eR^f$, $OR^g$, and CN wherein $R^a$ to $R^g$ are, independently of one another, H or $C_1$-$C_6$ alkyl or a heterocycle optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl, or $R^1$ and $R^2$ together represent a heterocycle optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$ $OR^g$, and CN wherein $R^a$ to $R^g$ are, independently of one another, H or $C_1$-$C_6$ alkyl, and $R^3$ is an aryl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl or a heteroaryl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl, as well as any stereoisomers, diastereoisomers, enantiomers and mixtures thereof and any pharmaceutically acceptable salts and/or solvates thereof, provided in said compound $R^3$ and X—$R^1$ groups are in trans position.

2. The method of claim 1, wherein in the compound of formula (1), $R^2$ is H or $CH_2OH$.

3. The method of claim 1, wherein in the compound of formula (1), X is O.

4. The method of claim 1, wherein in the compound of formula (1), $R^1$ is H or C(═O)—$C_1$-$C_6$ alkyl.

5. The method of claim 1, wherein the compound of formula (1) corresponds to the following formula (I'):

(I')

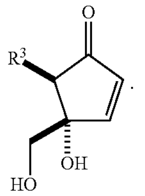

6. The method of claim 1, wherein in the compound of formula (1), $R^3$ is an aryl, optionally substituted with:

one or more groups selected from the group consisting of halogen, $C_1$-$C_6$ haloalkyl, $C_1$-$C_6$ alkyl, O—$C_1$-$C_6$alkyl, and CN, or two substituents together forming a heterocycle.

7. The method of claim 1, wherein the compound of formula (I) is selected from the following compounds:

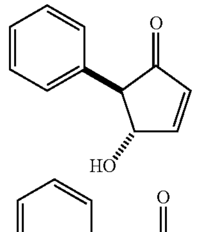
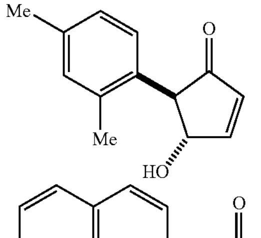
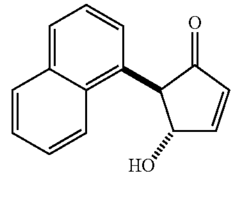
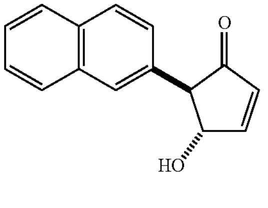

-continued
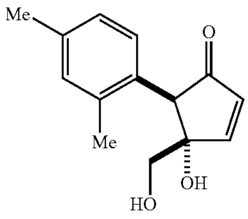
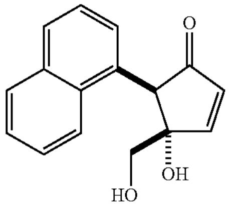
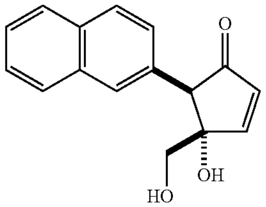
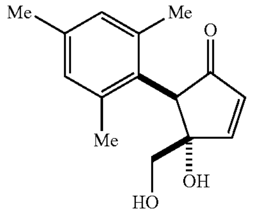
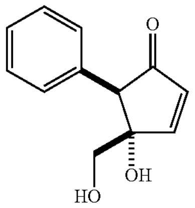
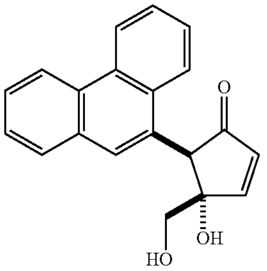
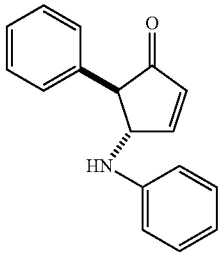
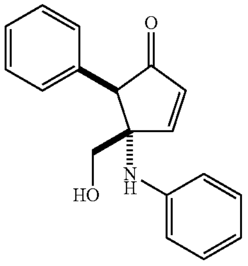
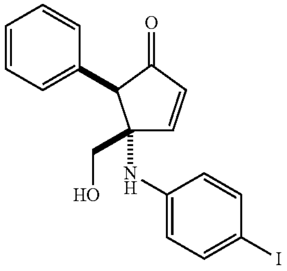
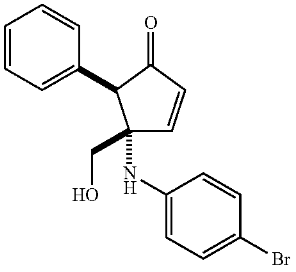
-continued
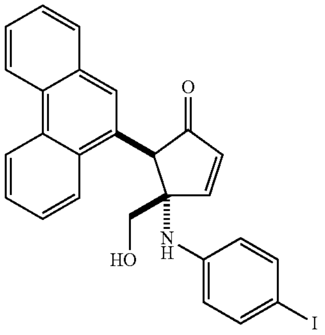
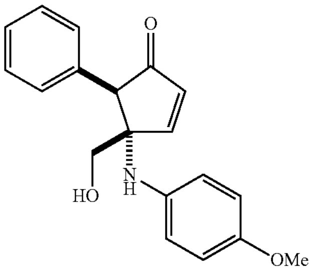
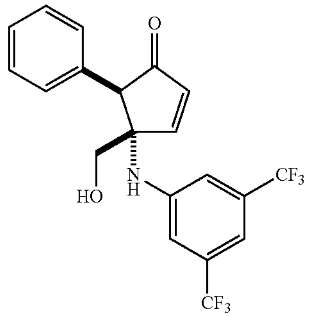
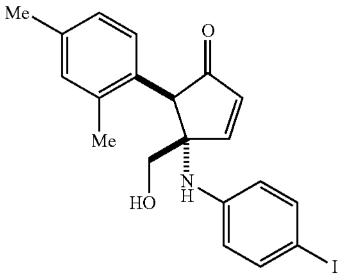
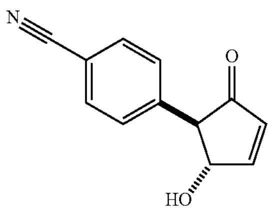
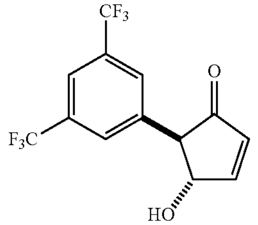
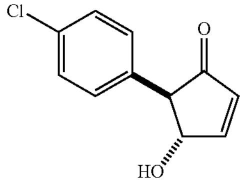

-continued
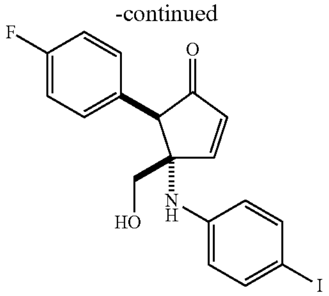
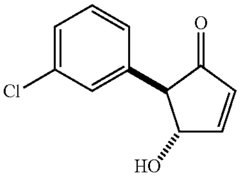
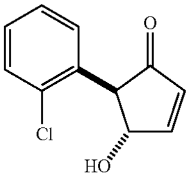
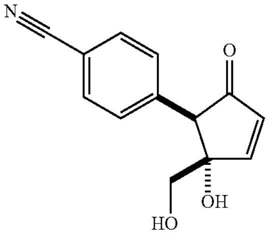
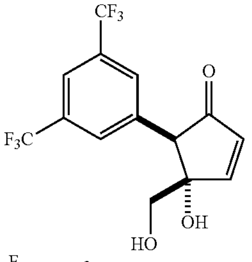
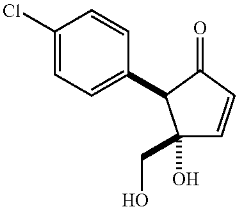
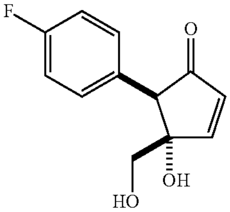
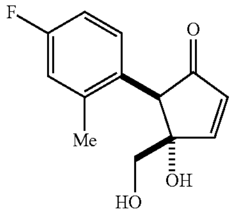
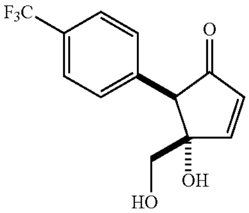
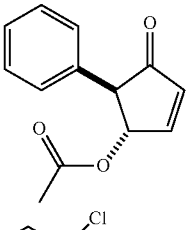
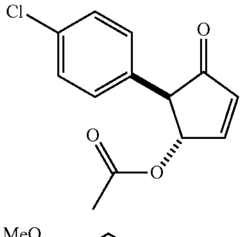
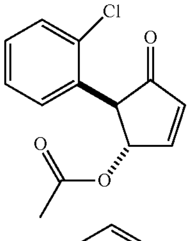
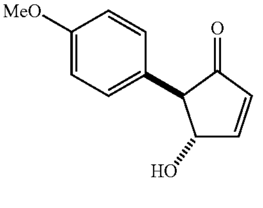
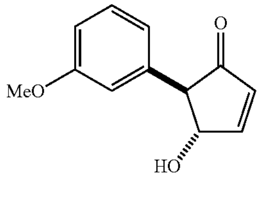
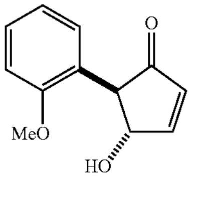
-continued
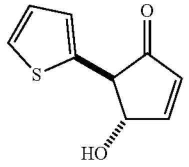
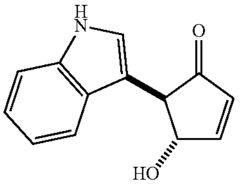
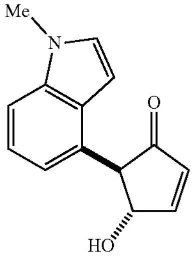
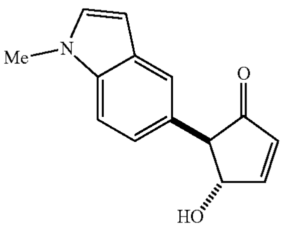
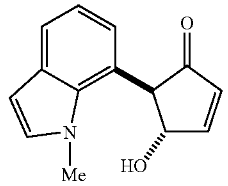
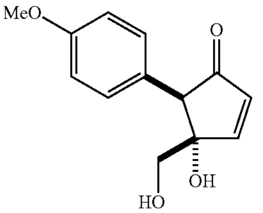
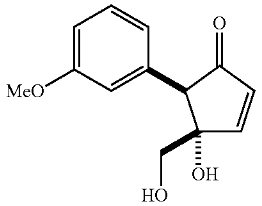
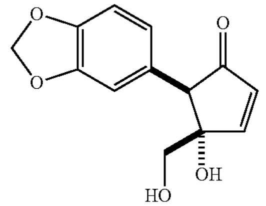
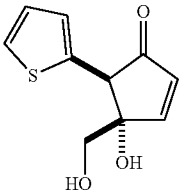
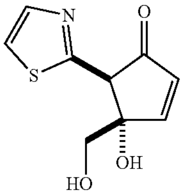
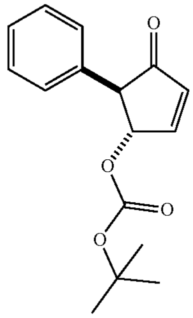
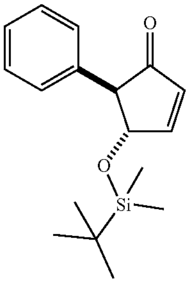
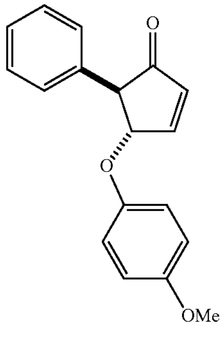
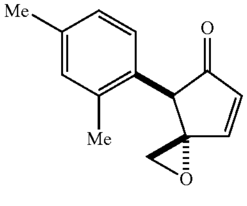

-continued

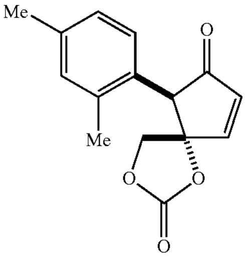

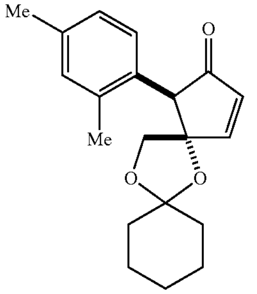

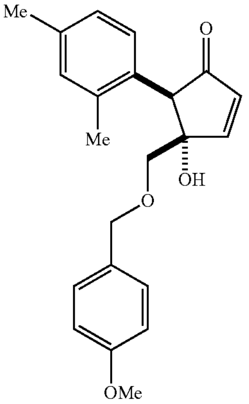

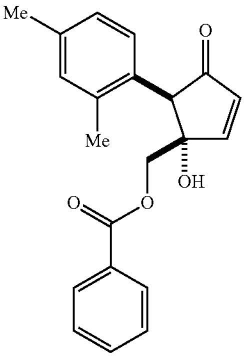

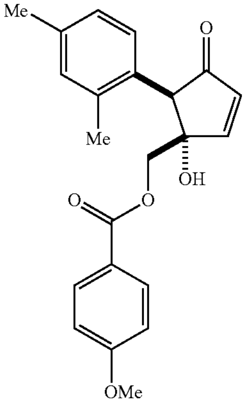

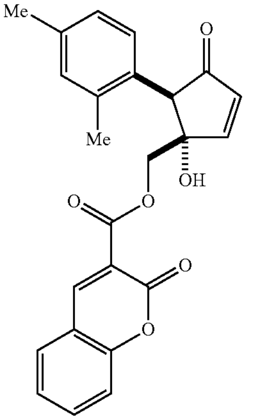

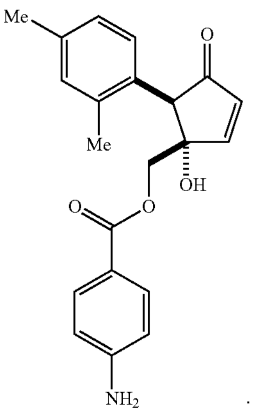

.

8. The method of claim 7, wherein the compound of formula (1) is selected from the group consisting of:

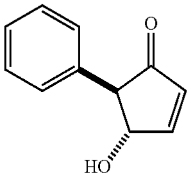
,
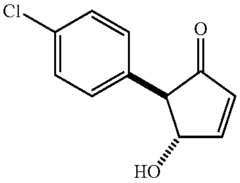
,
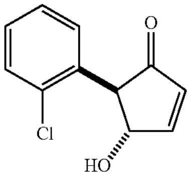
,
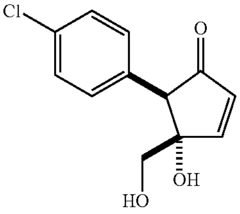
,
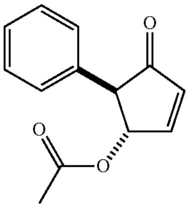
,
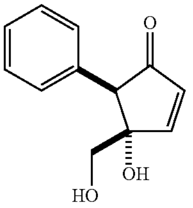
,
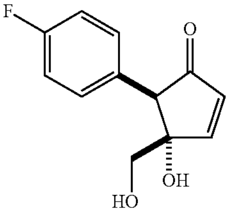
, and
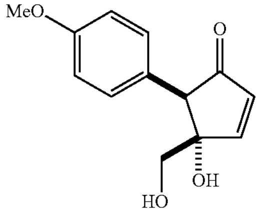
.

9. A pharmaceutical composition comprising a compound of the following formula (1)

(I)

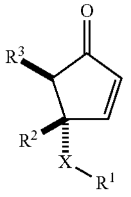

wherein

X is O or NH, $R^1$ is H, a phenyl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl, C(=O)—$C_1$-$C_6$ alkyl, C(=O)—O—$C_1$-$C_6$ alkyl or Si($C_1$-$C_6$ alkyl)$_3$, $R^2$ is H or $CH_2OR^4$, $R^4$ being H, $C_1$-$C_6$ alkyl, $C_1$-$C_6$ alkyl-aryl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl or C(=O)$R^5$, $R^5$ being an aryl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl or a heterocycle optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein Ra to $R^g$ are, independently of one another, H or $C_1$-$C_6$ alkyl, or $R^1$ and $R^2$ together represent a heterocycle optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^o$, $CO_2R^d$, $CONR^eR^f$, $OR^9$, and CN wherein $R^a$ to $R^g$ are, independently of one another, H or $C_1$-$C_6$ alkyl, and $R^3$ is an aryl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl or a heteroaryl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^9$, and CN wherein $R^a$ to $R^g$ are, independently of one another, H or $C_1$-$C_6$ alkyl as well as any stereoisomers, diastereoisomers, enantiomers and mixtures thereof and any pharmaceutically acceptable salts and/or solvates thereof, provided in said compound $R^3$ and X—$R^1$ groups are in trans position, and a pharmaceutically acceptable excipient.

10. The method of claim 1, wherein the bacterial infections are urogenital, respiratory, digestive, neuronal, or skin infections.

11. A compound of the following formula (I):

(I)

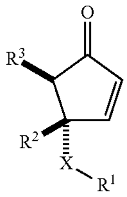

wherein

X is O or NH, $R^1$ is H, a phenyl optionally substituted with one or more substituents selected from halogen, $C_1$-$C_6$ alkyl, $C_3$-$C_7$ cycloalkyl, $C_1$-$C_6$ haloalkyl, oxo, $NR^aNR^b$, $COR^c$, $CO_2R^d$, $CONR^eR^f$, $OR^g$, and CN wherein $R^a$ to $R^g$ are, independently of one another, H or $C_1$-$C_6$ alkyl, C(═O)—$C_1$-$C_6$ alkyl, C(═O)—O—$C_1$-$C_6$ alkyl or Si($C_1$-$C_6$ alkyl$)_3$, $R^2$ is $CH_2OR^4$, $R^4$ being H, $C_1$-$C^6$ alkyl-aryl or C(═O)$R^5$ optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, indecently of one another, H or $C_1$-$C_6$ alkyl $R^5$ being an aryl optionally substate with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl or a heterocycle, optionally substate with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2$Rd, $CONR^eR^f$, $OR^g$, and ON wherein $R^a$ to $R^g$ are, independently of one another, H or $C_1$-$C_6$ alkyl and $R^3$ is an aryl optionally substituted with one or more substituents selected from halogen, $C_1$-$C_6$ alkyl, C3-C7 cycloalkyl, $C_1$-$C_6$ haloalkyl, oxo, $NR^aR^b$, $COR^c$, $CO_2R^d$, $CONR^eR^f$, $OR^g$, and ON wherein $R^a$ to $R^g$ are, independently of one another, H or $C_1$-$C_6$ alkyl or a heteroaryl optionally substituted with one or more substituents selected from halogen, $C_1$-$C_6$ alkyl, $C_3$-$C_7$ cycloalkyl, $C_1$-$C_6$ haloalkyl, oxo, $NR^aR^b$, $COR^c$, $CO_2R^d$, $CONR^eR^f$, $OR^g$, and CN wherein $R^a$ to $R^g$ are, independently of one another, H or $C_1$-$C_6$ alkyl, as well as any stereoisomers, diastereoisomers, enantiomers and mixtures thereof and any pharmaceutically acceptable salts and/or solvates thereof, provided in said compound $R^3$ and X—$R^1$ groups are in trans position, with the proviso that said compound is not:

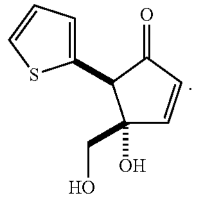 [SMILES: O=C1C=C[C@@](O)(CO)[C@H]1c1cccs1]

.

12. The compound of claim 11, wherein $R^2$ is $CH_2OH$ and/or X is O and/or $R^1$ is H or C(═O)—$C_1$-$C_6$ alkyl and/or $R^3$ is an aryl optionally substituted with one or more groups selected from halogen, $C_1$-$C_6$ haloalkyl, $C_1$-$C_6$ alkyl, O—$C_1$-$C_6$alkyl, and CN.

13. The compound of claim 11, having the following formula:

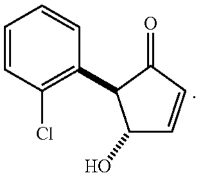 [SMILES: O=C1C=C[C@H](O)[C@H]1c1ccccc1Cl]

.

14. A method for the preparation of a compound of formula (I'):

(I')

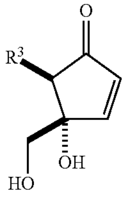

wherein $R^3$ is an optionally substituted aryl or an optionally substituted heteroaryl, or a pharmaceutically acceptable salt and/or solvate thereof, said method comprising the following steps:

(a) reacting a compound of formula (II-B)

(II-B)

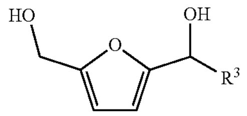

in which $R^3$ is an optionally substituted aryl or an optionally substituted heteroaryl, in presence of a $C_1$-$C_6$ alcohol, and optionally a Lewis acid, under a micro wave heating, (b) if necessary, isolating the diastereoisomer of formula (I').

15. The method of claim 4, wherein step (a) is achieved in presence of a Lewis acid.

16. The method of claim 4, wherein in the compound of formula (I), $R^1$ is H or C(=O)methyl.

17. The compound of claim 12, selected in the group consisting of:

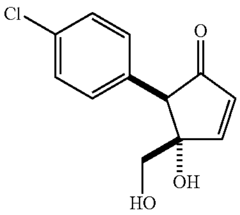
,
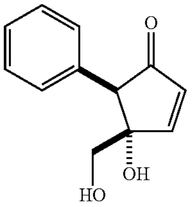
,
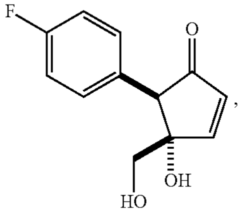
,
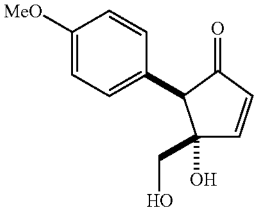
, and

-continued

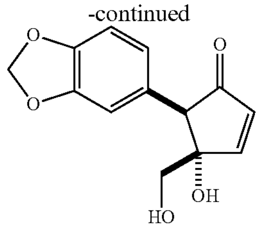
.

18. The compound of claim 17, being

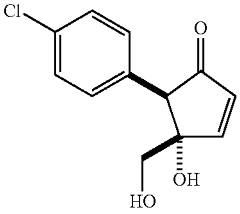
.

19. The method of claim 14, wherein in the compound of formula (I'), $R^3$ is an aryl, optionally substituted with:

one or more groups selected from the group consisting of halogen, $C_1$-$C_6$ haloalkyl, $C_1$-$C_6$ alkyl, O—C1-C6alkyl, and CN, or two substituents together forming a heterocycle.

20. The method of claim 14, wherein the Lewis acid is selected in the group consisting of DyCl3, $Dy(OTf)_3$, $Fe(OTf)_3$, $FeCl_3 \cdot 6H_2O$, $ZnCl_2$, $CuCl_2$, $Sc(OTf)_3$, and combinations thereof.

* * * * *